(12) United States Patent
Modlin et al.

(10) Patent No.: US 9,273,284 B2
(45) Date of Patent: Mar. 1, 2016

(54) METHOD FOR GENERATING POTENT DENDRITIC CELLS

(75) Inventors: Robert Lazarus Modlin, Sherman Oaks, CA (US); Mirjam Schenk, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 88 days.

(21) Appl. No.: 14/111,479

(22) PCT Filed: Apr. 16, 2012

(86) PCT No.: PCT/US2012/033811
§ 371 (c)(1),
(2), (4) Date: Nov. 15, 2013

(87) PCT Pub. No.: WO2012/142597
PCT Pub. Date: Oct. 18, 2012

(65) Prior Publication Data
US 2014/0056845 A1    Feb. 27, 2014

Related U.S. Application Data

(60) Provisional application No. 61/476,186, filed on Apr. 15, 2011.

(51) Int. Cl.
| | | |
|---|---|---|
| C12N 5/00 | (2006.01) |
| C12N 5/02 | (2006.01) |
| C12N 5/071 | (2010.01) |
| C12N 5/0784 | (2010.01) |
| A61K 35/15 | (2015.01) |
| A61K 38/20 | (2006.01) |
| A61K 39/39 | (2006.01) |
| A61K 39/00 | (2006.01) |

(52) U.S. Cl.
CPC .............. *C12N 5/0639* (2013.01); *A61K 35/15* (2013.01); *A61K 38/20* (2013.01); *A61K 39/39* (2013.01); *A61K 39/00* (2013.01); *A61K 2039/5154* (2013.01); *C12N 2501/2332* (2013.01)

(58) Field of Classification Search
None
See application file for complete search history.

(56) References Cited

U.S. PATENT DOCUMENTS

2004/0037807 A1   2/2004   Goldman
2007/0071719 A1   3/2007   Kim et al.

FOREIGN PATENT DOCUMENTS

WO    WO2010117848 A1    10/2010

OTHER PUBLICATIONS

O'Neill et al., 2004, J. Leuk. Biol. VOl. 75: 600-603.*
van de Loosdrecht et al., 1992, Canc. Immunother. vol. 34: 393-398.*
Netea et al., 2005, PNAS vol. 102: 16309-14.*
Schenk et al., 2012, Nat. Med. vol. 4: 555-564.*
Andreesen et al., 1998, Exp. Approaches Novel Ther. pp. 700-708.*
Son, "IL-32$_\gamma$ induces maturation of dendritic cells through a NF-kB/p38 MAPK signalling pathway", Day 3: 14th International Congress of Immunology Kobe, Japan, vol. 22 Suppl 1, Aug. 2010, Abstract No. PP-046-32 (p. iii30 Wednesday).

\* cited by examiner

*Primary Examiner* — Amy Juedes
(74) *Attorney, Agent, or Firm* — Pamela J. Sherwood; Bozicevic, Field & Francis LLP

(57) ABSTRACT

Highly potent dendritic cells are generated in vivo or ex vivo by exposing precursor cells to an effective dose of IL-32.

6 Claims, 22 Drawing Sheets a

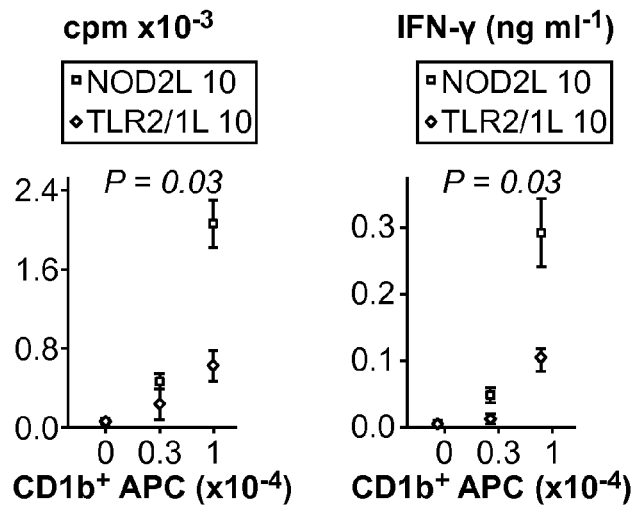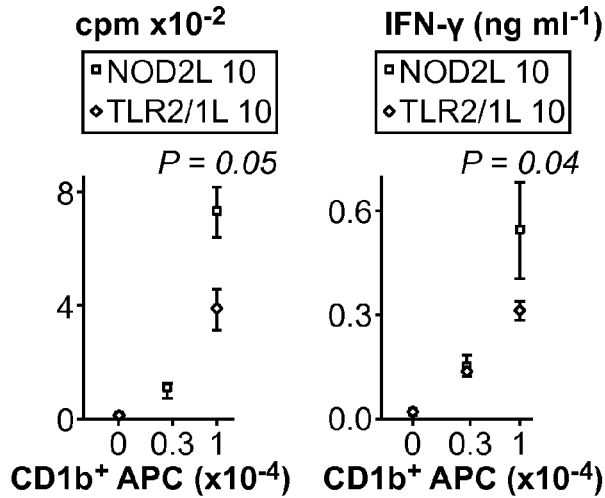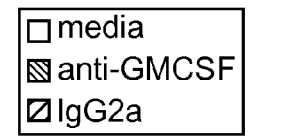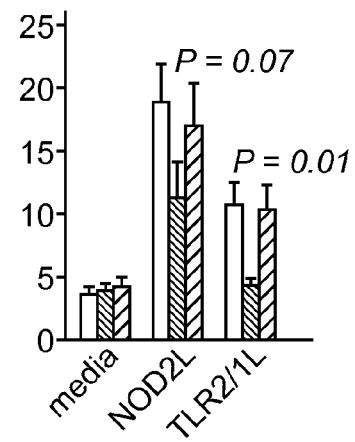
FIG. 14    FIG. 15

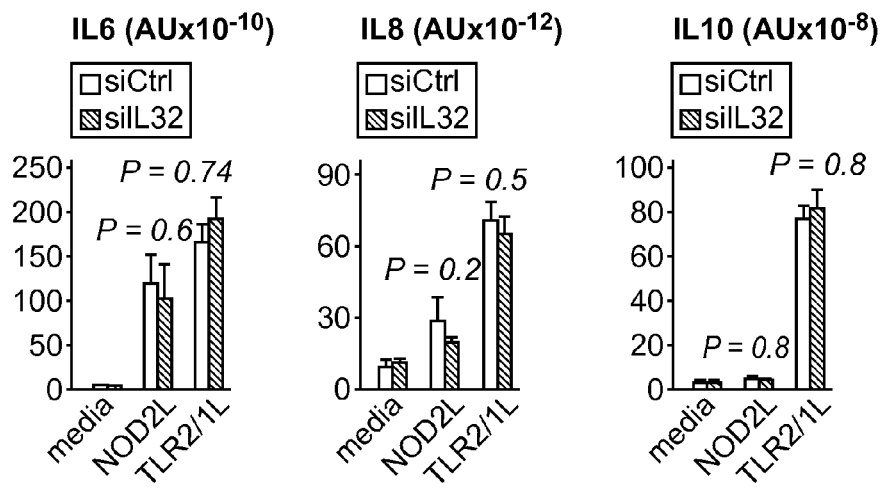
FIG. 16
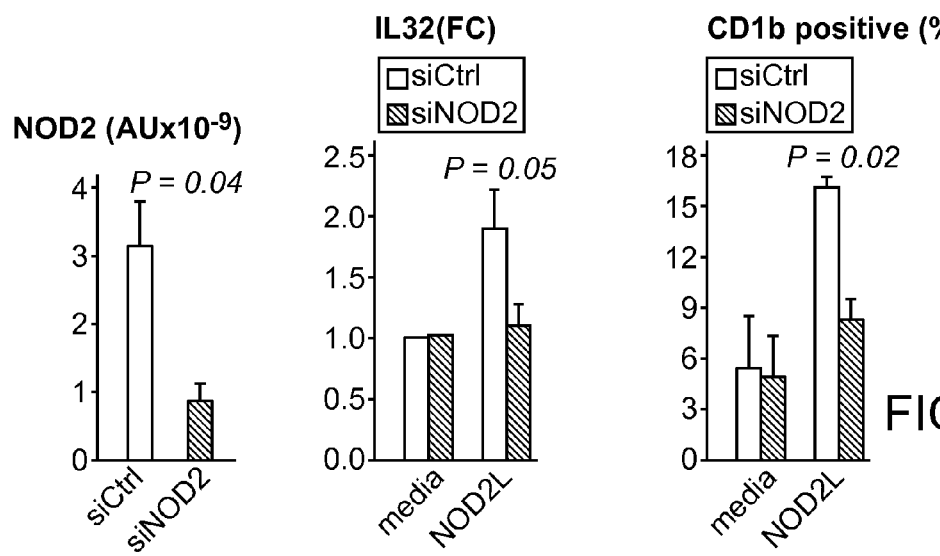
FIG. 17
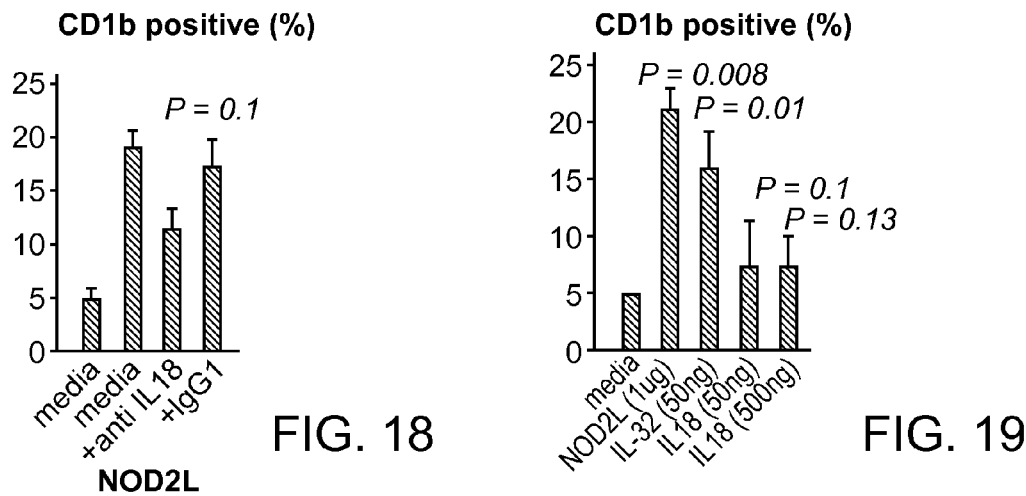
FIG. 18
FIG. 19

METHOD FOR GENERATING POTENT DENDRITIC CELLS

STATEMENT OF GOVERNMENT SUPPORT

This invention was made with Government support under AI022553, AR040312, and AI047868, awarded by the National Institutes of Health. The Government has certain rights in the invention.

BACKGROUND OF THE INVENTION

Dendritic cells (DCs) are antigen-presenting cells present in tissues in contact with the external environment, such as the skin and the inner lining of the nose, lungs, stomach and intestines. They can also be found in an immature state in the blood. Once activated, they migrate to the lymph nodes where they interact with T cells and B cells to initiate and shape the adaptive immune response.

Three major types of DCs have been previously defined in human blood: CD1c+ myeloid DCs, CD141+ myeloid DCs and CD303+ plasmacytoid DCs. Dendritic cells that circulate in blood do not have all the typical features of their counterparts in tissue, i.e. they are less mature and have no dendrites.

Immature dendritic cells constantly sample the surrounding environment for pathogens through pattern recognition receptors (PRRs) such as the toll-like receptors (TLRs). Such immature DC are competent phagocytes, taking up whole microorganisms and apoptotic cells for processing. Inflammatory stimuli, such as the local release of interferon-γ or lipopolysaccharide, induce the maturation of DC precursors, causing them to lose the ability to acquire further antigens but inducing their migration via the draining lymphatics to the secondary lymphoid organs. Simultaneously, they upregulate cell-surface receptors that act as co-receptors in T-cell activation such as CD80 (B7.1), CD86 (B7.2), and CD40, greatly enhancing their ability to activate T-cells. They also upregulate CCR7, a chemotactic receptor that induces the dendritic cell to travel through the blood stream to the spleen or through the lymphatic system to a lymph node where they act as antigen-presenting cells. It is believed that only dendritic cells can activate naïve T cells through the T cell antigen receptor—a function of the co-stimulatory molecules they express upon maturation, of which CD40, ICAM-1 (CD54), B7-1 (CD80) and B7-2 (CD86) are examples.

Myeloid dendritic cells are believed to arise from monocytes, which in turn are formed from stem cells in the bone marrow. Monocyte-derived dendritic cells are conventionally generated in vitro from monocytes or peripheral blood mononuclear cells (PBMCs) by treatment with interleukin 4 (IL-4) and granulocyte-macrophage colony stimulating factor (GM-CSF), leading to differentiation to immature dendritic cells (iDCs), and subsequent treatment with tumor necrosis factor (TNF) to differentiate into mature dendritic cells.

The promise that dendritic cells hold for use in a therapeutic setting makes their culture and analysis of great interest for clinical and research purposes.

SUMMARY OF THE INVENTION

Methods for the generation in vivo or ex vivo of highly potent dendritic cells are provided. In the methods of the invention a precursor of dendritic cells, e.g. monocytes, PBMCs, or the like that are not themselves dendritic cells, are exposed to a dose of IL-32 that is effective in inducing precursors to differentiate into dendritic cells. The exposure is optionally performed in the absence of cytokines such as IL-4 and GM-CSF. The dendritic cells thus generated may be characterized by expression of dendritic cell markers, such as CD86, CD1b, etc. Dendritic cells induced by activation of precursors with IL-32 are potent antigen presenting cells, particularly for Class I restricted antigens, and find use, for example, in the activation of resting or naïve T cells.

In some embodiments of the invention, IL-32 is used to generate potent DC ex vivo for clinical or research purposes, e.g. infusion into patients, studying antigen presentation pathways, etc. The ex vivo cultures may be exposed to IL-32 for a period of at least about one day, at least about 2 days, at least about 3 days or more. Exposure may be in the absence or presence of an effective dose of an antigen of interest, which antigens include without limitation pathogen antigens, such as mycobacterial antigens; tumor cell antigens; and the like. For clinical purposes the dendritic cells may be autologous relative to a patient, or may be allogeneic, xenogeneic, etc. Following generation of dendritic cells the cells are optionally purified prior to infusion into patients, e.g. sorted by any suitable affinity method, such as flow cytometry, magnetic sorting, affinity columns, and the like. In some embodiments the cells are sorted for expression of markers associated with dendritic cells, which can include CD1b, CD40, MHC class I, MHC class II, CD80 and CD86CD11b. For example, CD11b$^+$ cells can be selected for infusion into a patient.

In other embodiments of the invention, a effective dose of IL-32 is delivered to an individual, optionally in combination with antigen, to differentiate precursors into dendritic cells. The IL-32 may be delivered locally or systemically, and over a period of time sufficient to provide for the dendritic cell differentiation. Individuals of interest may benefit from the enhanced activation of T cells, e.g. for treatment of cancer; treatment of infectious diseases, including without limitation mycobacterial infections, chronic viral infections, and the like.

The identification herein of a role for IL-32 in the differentiation of monocytes into DCs provides a new mechanism of innate immunity, e.g. to microbial pathogens, cancer antigens, etc. In addition to inducing monocytes to differentiate into DCs, IL-32 also contributes to the maturation of DCs.

Figure 1:
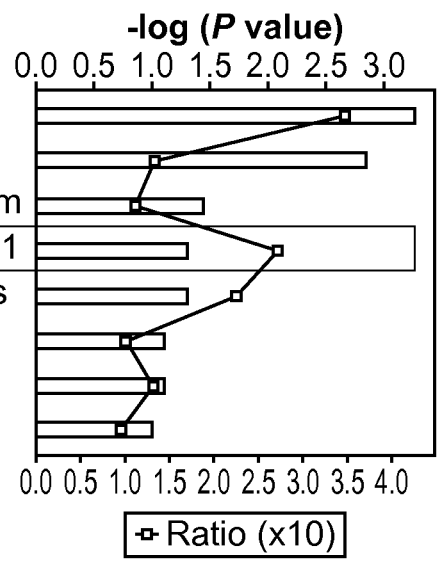
FIG. 1. NOD2L and TLR2/1L induce functionally divergent DC-specific pathways. Human monocytes, activated with either NOD2L (1 µg ml$^{-1}$) or TLR2/1L (1 µg ml$^{-1}$), were analyzed for their gene expression profiles using Affymetrix microarrays. (a) Ingenuity pathway analysis to associate functional pathways with the corresponding gene sets by enrichment ratios and P values; P values were corrected for multiple hypothesis testing using the Benjamini-Hochberg method. RAN, ras-related nuclear protein; TC, T cell; GR, glucocorticoid receptor; PPAR, peroxisome proliferator—associated receptor; NF-κB, nuclear receptor-κB. (b) Enrichment analysis of the induced gene sets with the four DC-specific pathways, shown as the percentage of genes that are induced within each pathway and the corresponding P value. (c) Differential gene expression profile of the microbial ligand activated monocytes, illustrated as the fold change ratio (FC) of NOD2L/medium on the x axis and TLR2/1L/medium on the y axis.
Figure 1:
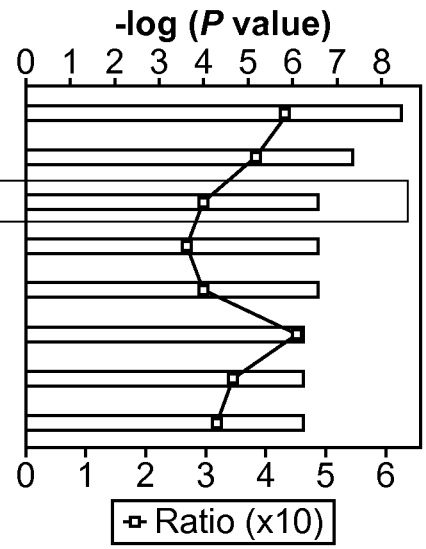
Figure 1:
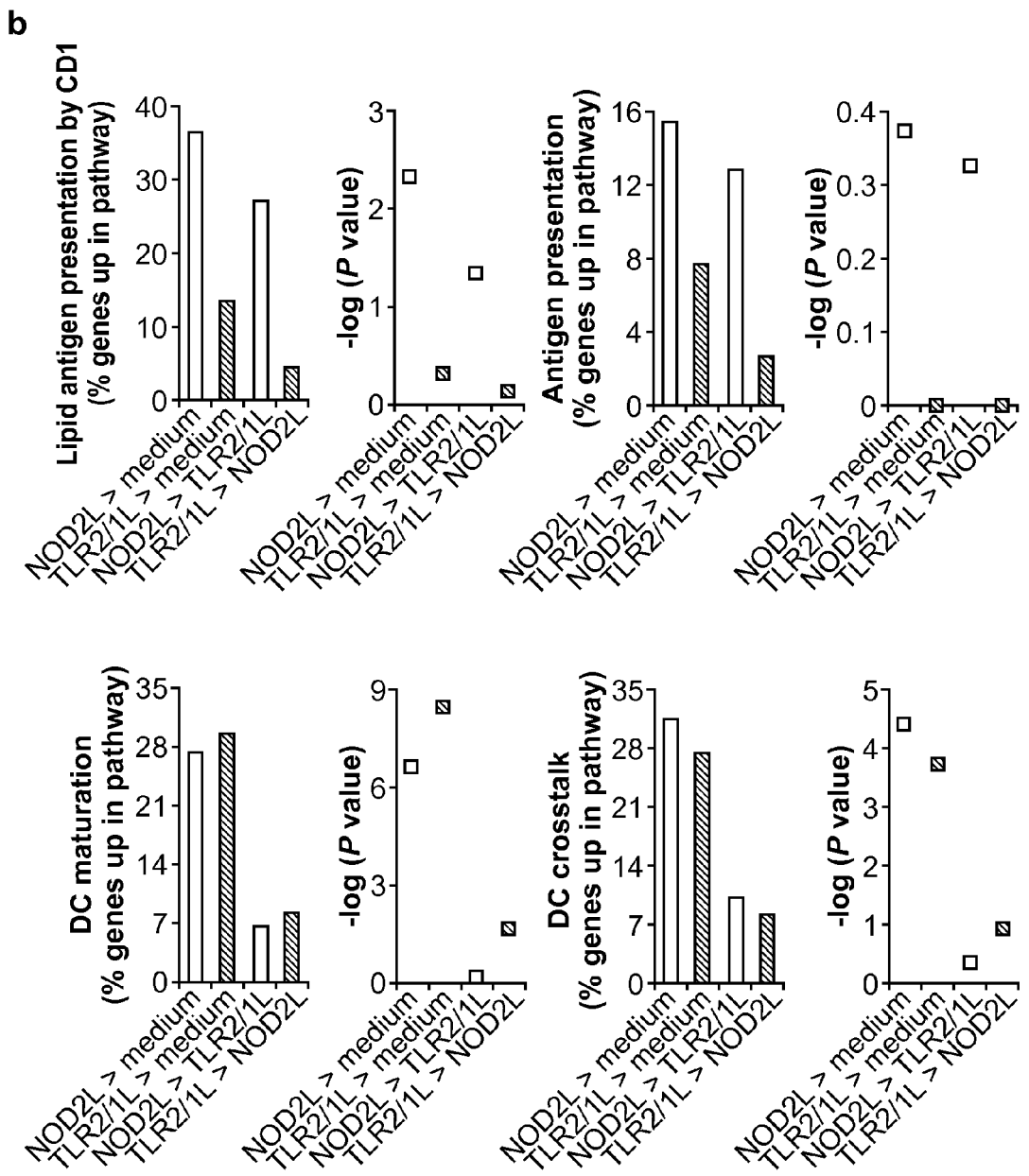

Induction of DC was performed at 1 μg ml$^{-1}$ for both NOD2L and TLR2/1L (left). A representative flow cytometry staining for CD1b is shown before and after MACS purification for CD1b+ DC. (right) Surface expression of markers involved in antigen presentation was assessed by flow cytometry, gated on CD1b+ MACS sorted DC. Data are indicated as mean MFI+/−SEM, n=4. Statistical significance was calculated by paired two-tailed Students t-test.

FIG. 14. Functional differences between the NOD2L- and TLR2/1L-induced DC at supraoptimal doses. NOD2L (10 µg ml$^{-1}$) or TLR2/1L (10 µg ml$^{-1}$) induced purified CD1b+ DC were tested to stimulate a T cell response in the context of tetanus toxoid and Influenza peptide M1 and autologous CD8+ T-cells. Proliferation is measured as $^3$H-thymidine incorporation and IFN-γ secretion. Data are representative of triplicate wells of three independent experiments +/−SEM. Statistical significance was calculated by two-tailed Students t-test.

FIG. 15. NOD2L induction of CD1b+ DC is only partially GM-CSF dependent. Purified human monocytes were activated with either NOD2L (1 µg ml$^{-1}$) or TLR2/1L (1 µg ml$^{-1}$) in the absence (media) or presence of neutralizing anti-GMCSF mAb (10 µg ml$^{-1}$) or control IgG2a (10 µg ml$^{-1}$). At 48 hours cells were harvested and analyzed by flow cytometry for the expression of CD1b. Data are shown as mean+/−SEM, n=4. Two tailed Student t-test was used to calculate the P-value for differences between anti-GM-CSF and control IgG2a treated monocytes.

FIG. 16. siRNA knockdown of IL32 does not directly affect NOD2L- and TLR2/1L-induced cytokine mRNA levels. Monocytes were transfected with siRNA for IL32 or ctrl siRNA and subsequently analyzed for NOD2L (1 µg ml$^{-1}$) and TLR2/1L (1 µg ml$^{-1}$) induced IL6, IL8 and IL10 mRNA at 6 h. Data are represented as mean+/−SEM, n=4. Statistical significance was calculated by two-tailed Students t-test.

FIG. 17. siRNA knockdown of NOD2 blocks response to NOD2L. Monocytes were transfected with siRNA for NOD2 or ctrl siRNA (left panel) and subsequently analyzed for NOD2L (1 µg ml$^{-1}$) induction of IL-32 (middle panel) and CD1b (right panel). Data are represented as mean+/−SEM, n=3. Statistical significance was calculated by two-tailed Students t-test.

FIG. 18. NOD2L induction of CD1b+ DC is not significantly blocked by neutralizing IL-18. Purified human monocytes were activated with NOD2L (1 µg ml$^{-1}$) in the absence (media) or presence of neutralizing anti-IL-18 mAb (10 µg ml$^{-1}$) or control IgG1 (10 µg ml$^{-1}$). At 48 hours cells were harvested and analyzed by flow cytometry for the expression of CD1b. Data are shown as mean+/−SEM, n=3. Two tailed Student t-test was used to calculate the P-value for differences between anti-IL-18 and control IgG treated monocytes.

FIG. 19. IL-18 alone is not sufficient to induce DC differentiation. Purified human monocytes were activated with either NOD2L (1 µg ml$^{-1}$), IL-32 (50 ng ml$^{-1}$), or IL-18 (50 ng ml$^{-1}$, 500 ng ml$^{-1}$) for 48 hours and analyzed by flow cytometry for the expression of CD1b (DC marker). Data are shown as mean+/−SEM, n=3. Statistical significance was calculated by two tailed Students t-test.

Figure 20:
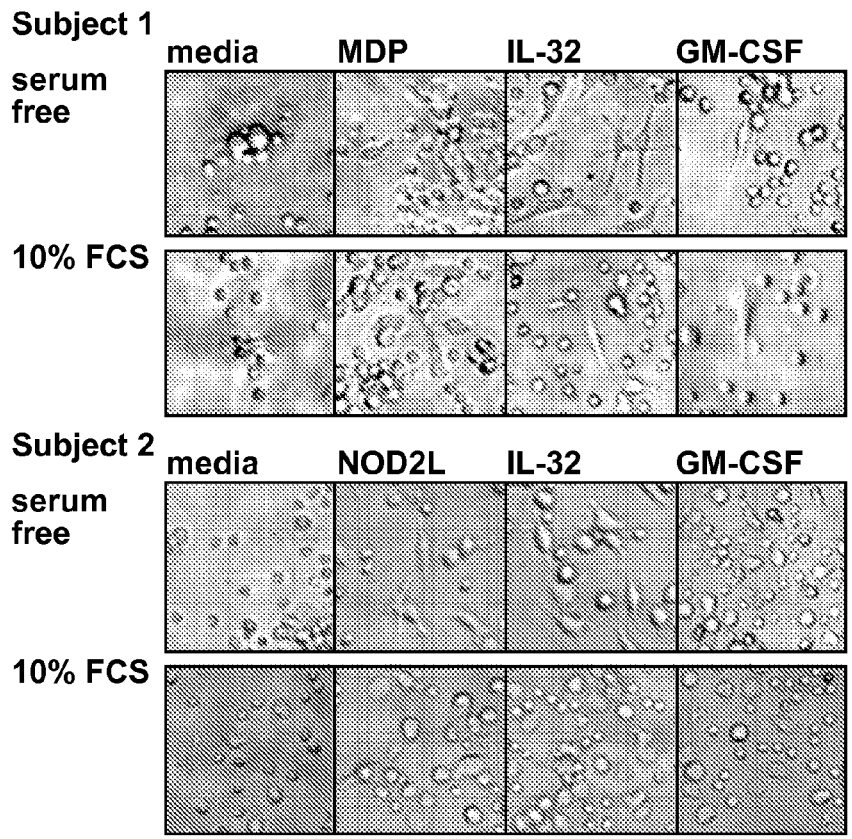

FIG. 20. IL-32-induced DC morphology is not serum dependent. Human monocytes were activated with either NOD2L (1 µg ml$^{-1}$), IL-32 (50 ng ml$^{-1}$) or GM-CSF (1 U ml$^{-1}$) in either serum free media or in 10% FCS. At day 3 cell morphology was investigated. Two representative donors for each condition are shown.

Figure 21:
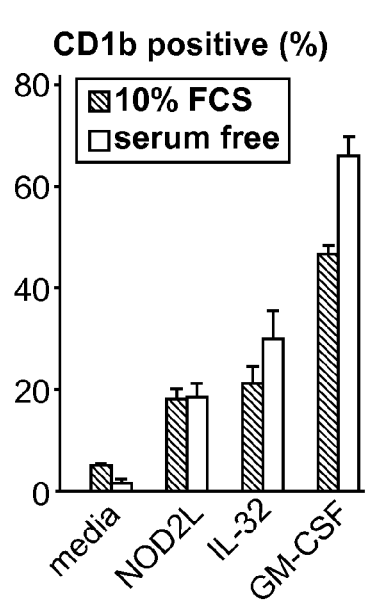

FIG. 21. IL-32-induced CD1b+ DC differentiation is not serum dependent. Human monocytes were activated with either NOD2L (1 µg ml$^{-1}$), IL-32 (50 ng ml$^{-1}$) or GM-CSF (1 U ml$^{-1}$) in either serum free media or in 10% FCS. At day 3 cells were harvested and analyzed by flow cytometry for the expression of CD1b. Data are shown as mean+/−SEM, n=4.

Figure 22:
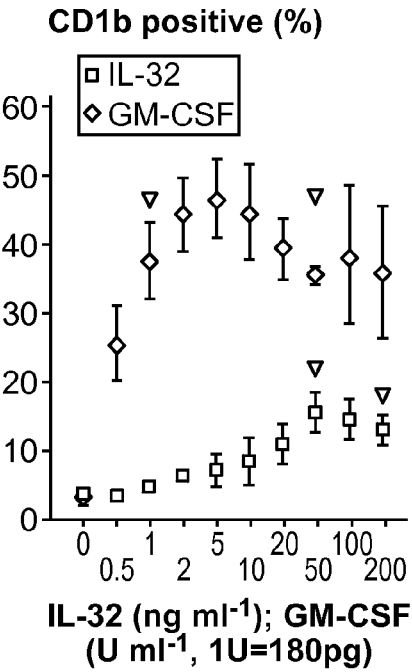

FIG. 22. Dose titration of IL-32 and GM-CSF for induction of CD1b+ DC. Purified human monocytes were activated with either IL-32 (ng ml$^{-1}$) or GM-CSF (U ml$^{-1}$) at various concentrations for 48 hours and analyzed by flow cytometry for the expression of CD1b+ DC. Data are shown as mean+/−SEM, n=4. Statistical significance was calculated by two-tailed Students t test and showed significant higher induction of CD1b+ DC by GM-CSF at concentrations 0.5 U ml$^{-1}$ and higher.

Figure 23:
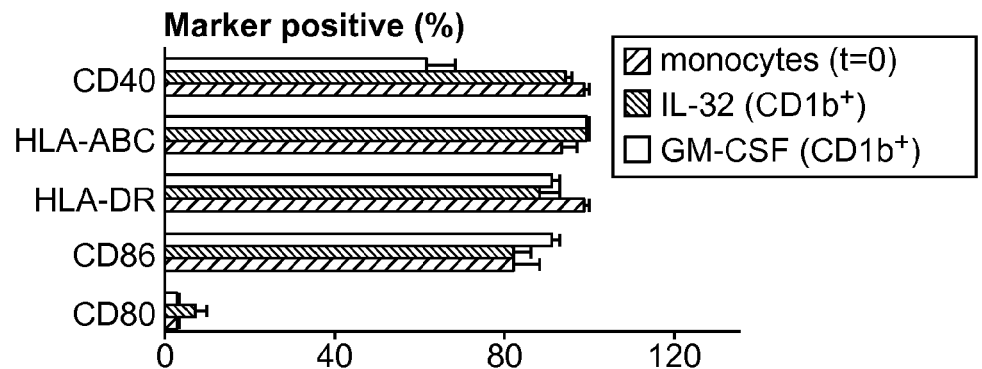

FIG. 23. IL-32 is a potent inducer of functional CD1b+ DC. Purified human monocytes were activated with either IL-32 (50 ng ml$^{-1}$) or GM-CSF (1 U ml$^{-1}$) for 48 hours. Surface expression of markers involved in antigen presentation was assessed by flow cytometry, gated on CD1b+ DC induced by either IL-32 or GM-CSF; data are indicated as mean percentage positive, +/−SEM, n=6. Two-tailed Students t test showed no statistical significant differences between the IL-32 and GM-CSF-induced DC in percentage marker positive cells.

Figure 24:
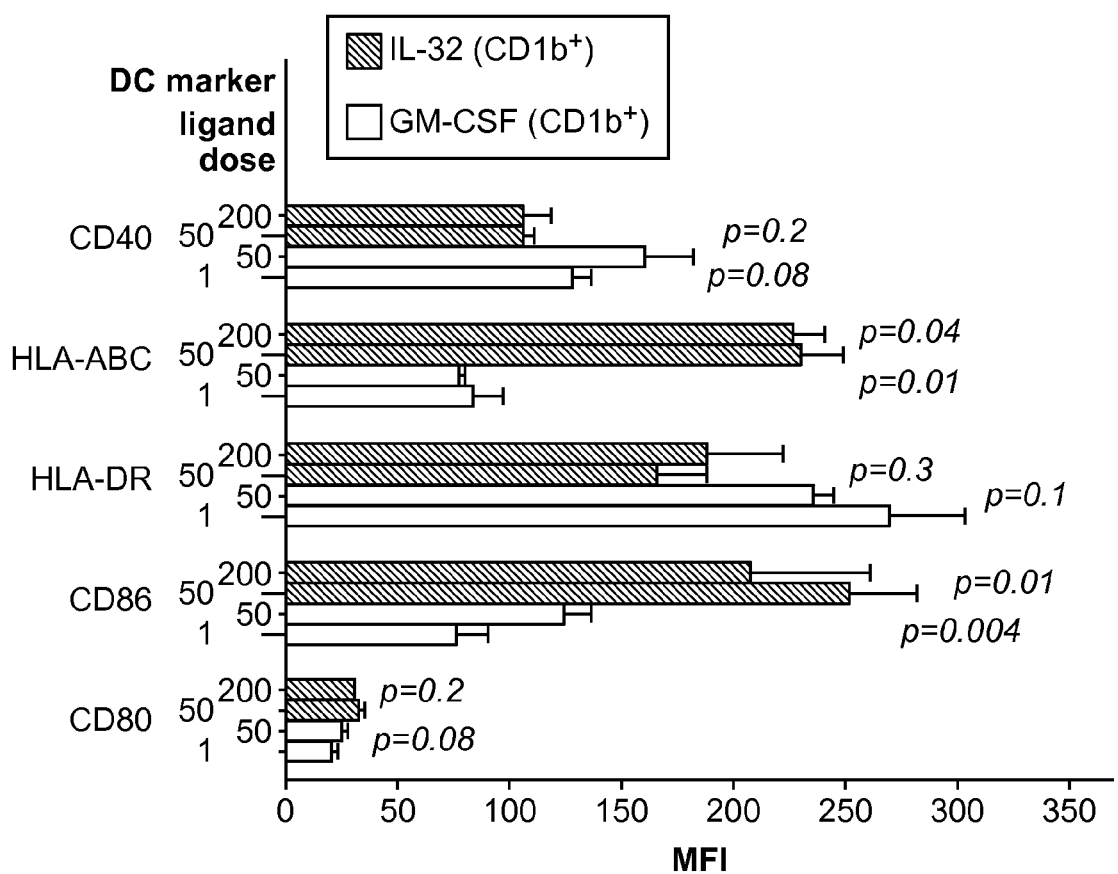

FIG. 24. Phenotypic differences between the IL-32- and GMCSF-induced DC at optimal and supraoptimal doses. Surface expression of markers involved in antigen presentation was assessed by flow cytometry, gated on CD1b+ DC. Induction of DC was performed at optimal and supraoptimal doses of IL-32 (50 ng ml$^{-1}$, 200 ng ml$^{-1}$) or GM-CSF (1 U ml$^{-1}$, 50 U ml$^{-1}$); data are indicated as mean MFI+/−SEM, n=6. Statistical significance was calculated by paired two-tailed Students t-test.

Figure 25:
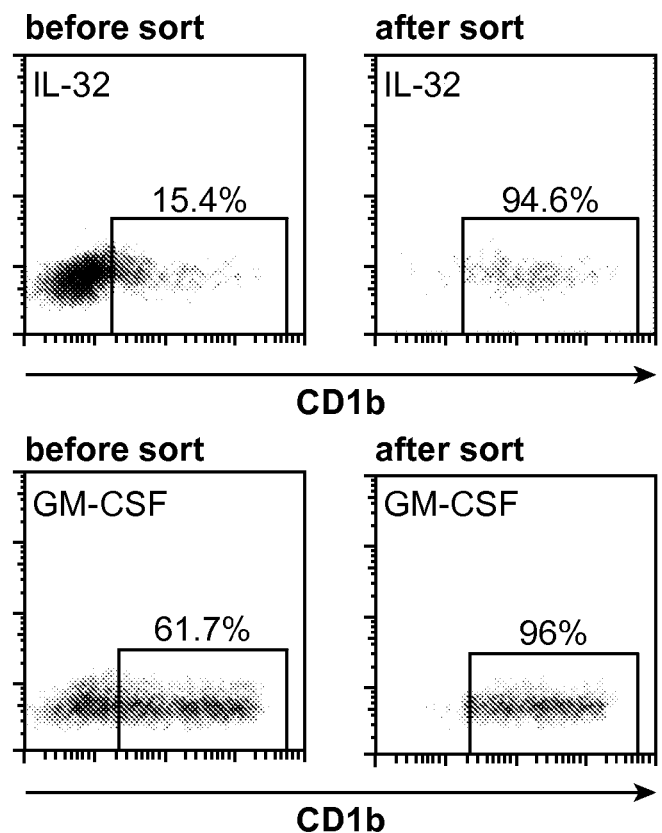
Figure 25:
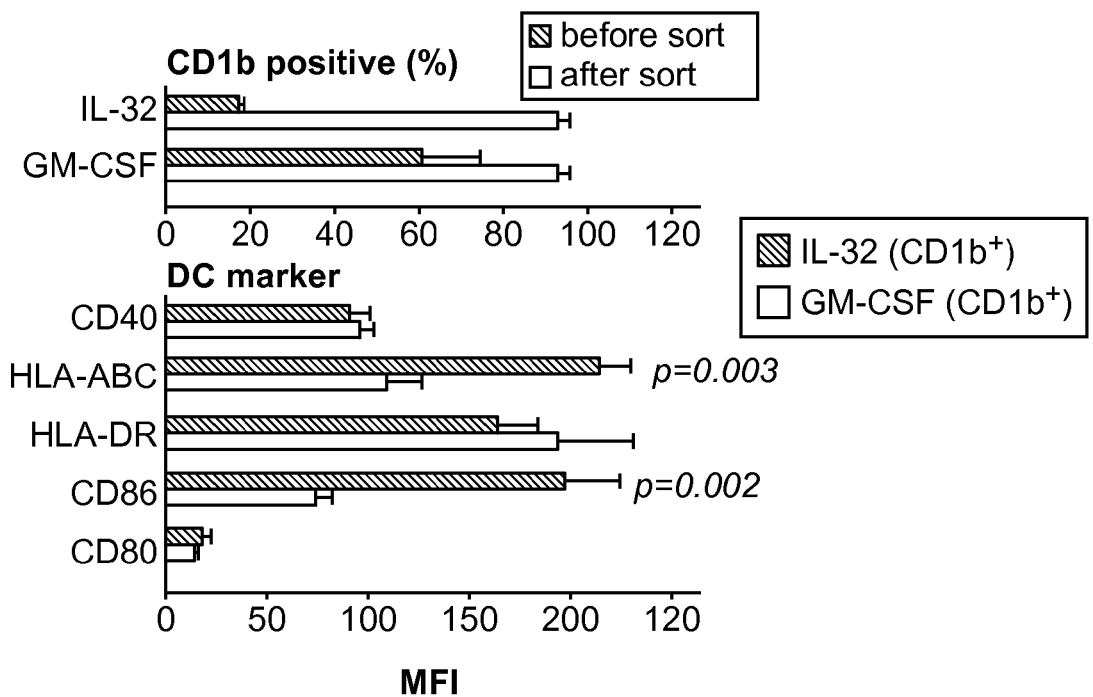

FIG. 25. Phenotypic characterization of purified NOD2L- and TLR2/1L-induced DC. Induction of DC was performed at 50 ng ml$^{-1}$ for IL-32 and 1 U ml$^{-1}$ for GM-CSF. (left) A representative flow cytometry staining for CD1b is shown before and after MACS purification for CD1b+ DC. (right) Surface expression of markers involved in antigen presentation was assessed by flow cytometry, gated on CD1b+ MACS sorted DC. Data are indicated as mean MFI+/−SEM, n=4. Statistical significance was calculated by paired two-tailed Students t-test.

Figure 26:
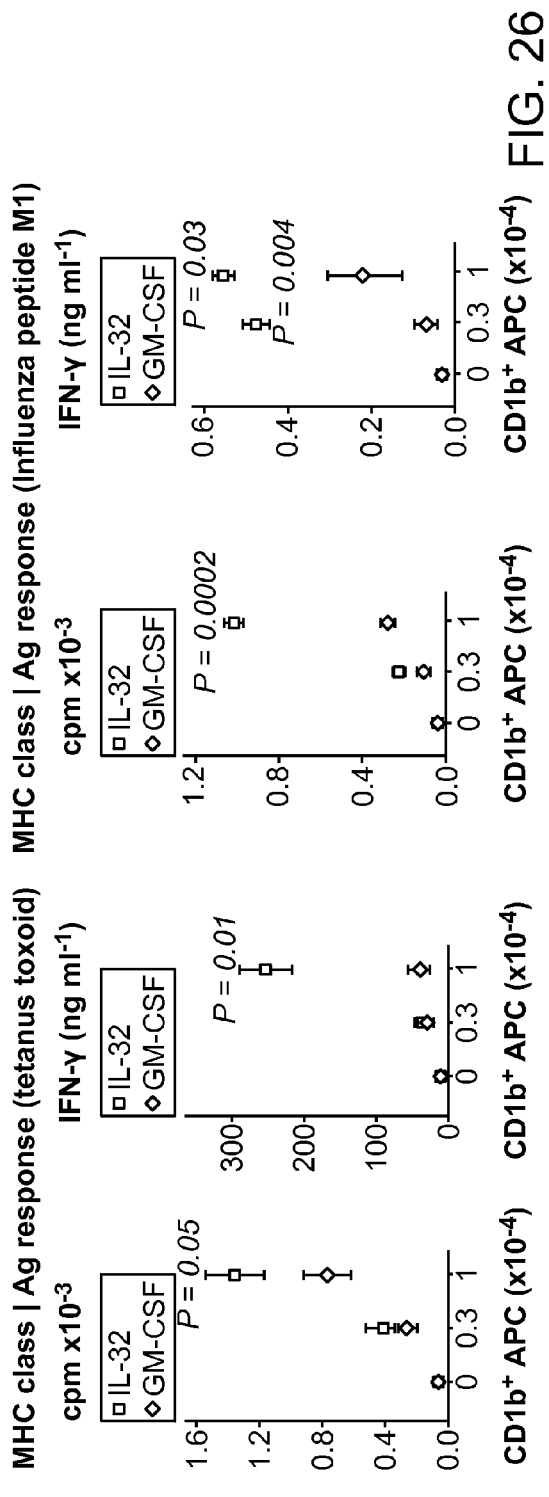

FIG. 26. Functional differences between the IL-32- and GM-CSF-induced DC at supraoptimal doses. IL-32 (200 ng ml$^{-1}$) or GM-CSF (50 U ml$^{-1}$) induced purified CD1b+ DC were tested to stimulate a T cell response in the context of tetanus toxoid and Influenza peptide M1 and autologous CD8+ T-cells. Proliferation is measured as $^3$H-thymidine incorporation and IFN-γ secretion. Data are representative of triplicate wells of three independent experiments +/−SEM. Statistical significance was calculated by two-tailed Students t-test.

Figure 27:
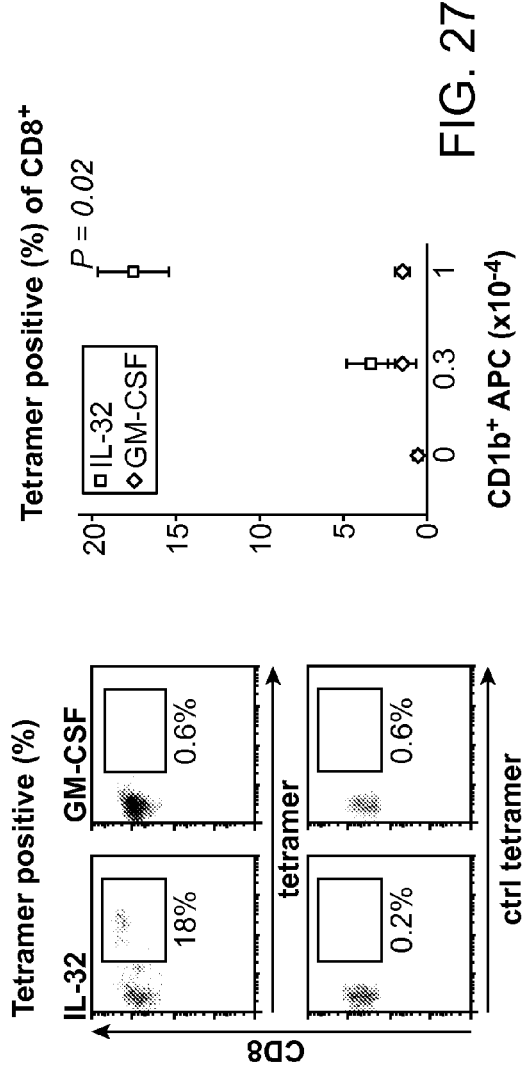

FIG. 27. Functional differences between the IL-32- and GM-CSF-induced DC at supraoptimal doses. IL-32 (200 ng ml$^{-1}$) and GM-CSF (50 U ml$^{-1}$) induced purified CD1b+ DC were tested to stimulate a T cell response in the context of Influenza peptide M1 (GILGFVFTL) and autologous CD8+ T-cells. At day 15 CD8+ T-cells were analyzed by staining using specific tetramers (PE-HLA-A*0201 Influenza-M1 (GILGFVFTL), Beckman Coulter) as recommended by the manufacturer. (left) A representative flow staining is shown gated on CD8+ cells (y-axis) and stained with specific tetramers and ctrl tetramers (x-axis). (right) Data are representative of triplicate wells of two independent experiments +/−SEM. Statistical significance was calculated by two-tailed Students t-test.

Figure 28:
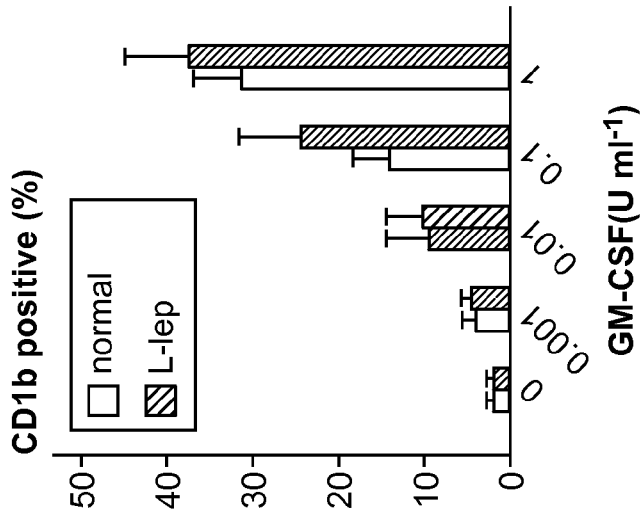

FIG. 28. Isotype controls for Immunolabeling of IL-32 and NOD2. Immunoperoxidase labeling on leprosy skin lesions was performed using isotype controls for monoclonal antibodies against IL-32 (IgG2a, A11C9, YbdYbiotech) and NOD2 (IgG1, 2D9, Thermo Scientific).

Figure 29:
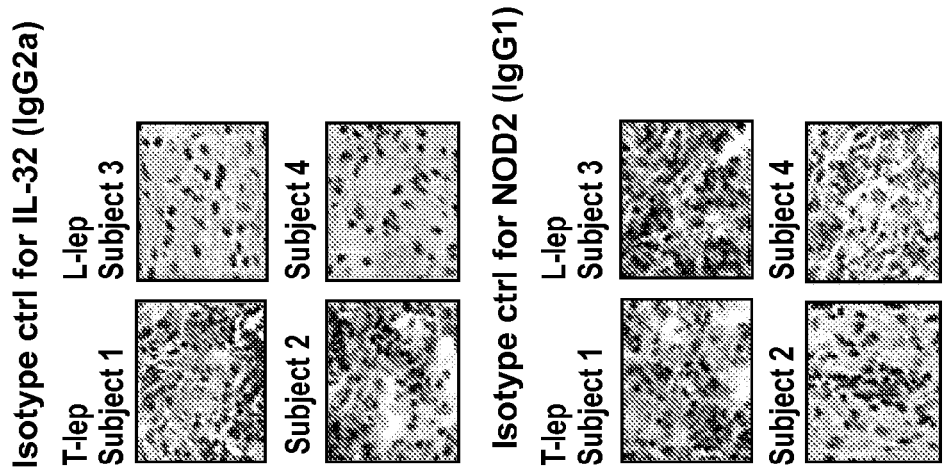

FIG. 29. Monocytes from L-lep patients respond to GM-CSF. Monocytes from L-lep patients were compared to healthy donors for their response to GM-CSF at various doses. Cells were harvested at 48 hours and analyzed by flow cytometry for the expression of CD1b. Data are shown as mean+/−SEM, n=3. No Statistical significant differences were observed using two-tailed Students t-test.

Figure 30:
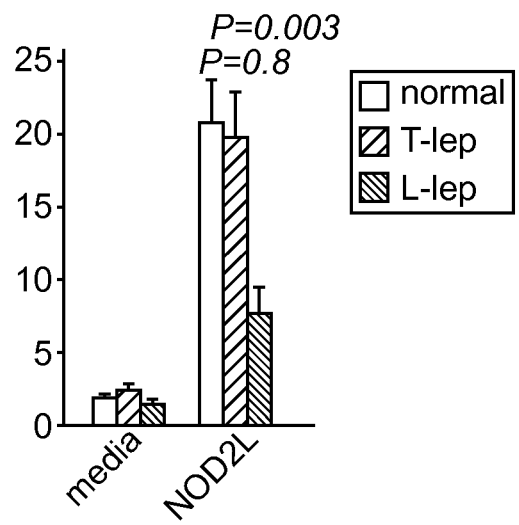

FIG. 30. Monocytes from L-lep but not Tlep patients show reduced induction of CD1b$^+$ DC in response to NOD2L. Monocytes from T-lep and L-lep patients were compared to healthy donors for their response to NOD2L (1 µg ml$^{-1}$). Cells were harvested at 48 h and analyzed by flow cytometry for the expression of CD1b. Data are shown as mean+/−SEM, n≥6. Statistical significance was calculated by two-tailed Students t-test.

Figure 31:
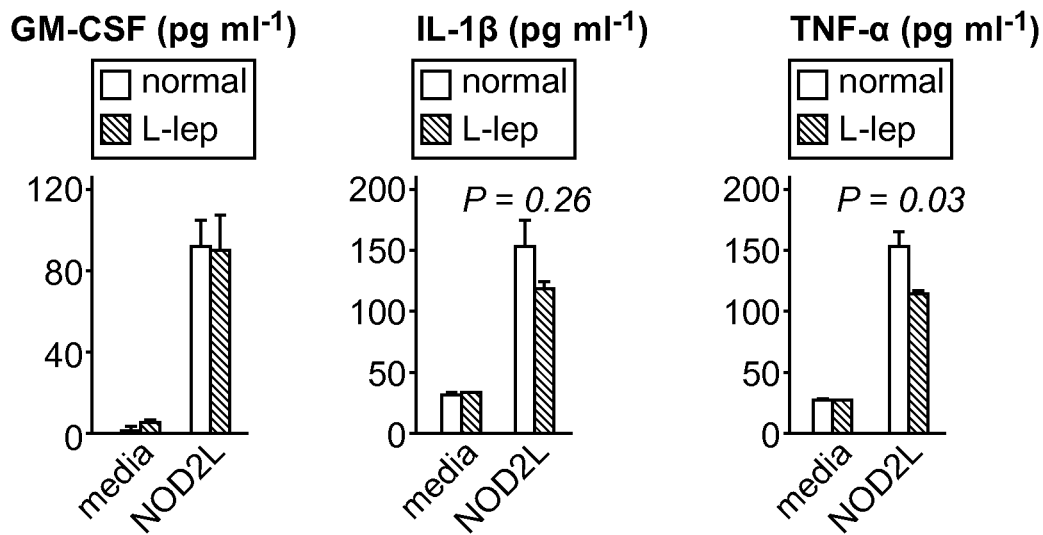

FIG. 31. Induction of cytokines in monocytes from L-lep patients in response to NOD2L. Monocytes from L-lep patients were compared to healthy donors for their cytokine response to NOD2L (1 µg ml$^{-1}$). Supernatants were harvested at 24 h and protein levels of GM-CSF, IL-1β and TNF-α were determined. data are shown as mean+/−SEM, n≥6. Statistical significance was calculated by two-tailed Students t-test.

DETAILED DESCRIPTION OF THE EMBODIMENTS

Methods are provided for the generation in vivo or ex vivo of highly potent dendritic cells by exposing suitable precursor cells, usually monocytes or precursors thereof, to an effective dose of IL-32. The dendritic cells thus generated may be characterized by expression of dendritic cell markers, such as CD86, CD1b, etc. Dendritic cells induced by activation of precursors with IL-32 are potent antigen presenting cells, particularly for Class I restricted antigens, and find use, for example, in the activation of resting or naïve T cells.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having a condition in which increased immune responsiveness is desirable, including infection, e.g. chronic infection, cancer, and the like. Subjects may be human, but also include other mammals, particularly those mammals useful as laboratory models for human disease, e.g. mouse, rat, etc.

As used herein, the terms "treatment," "treating," and the like, refer to administering an agent, or carrying out a procedure (e.g., immunization, infusion of dendritic cells, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration of a condition, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

Interleukin-32 (IL-32) is a recently described cytokine produced mainly by NK cells, T lymphocytes, epithelial cells, and blood monocytes stimulated by IL-2 or IFN-γ, that is a strong inducer of pro-inflammatory cytokines such as tumor necrosis factor (TNF)-α, IL-1β, IL-6, and IL-8, and macrophage inflammatory protein-2 (MIP-2). More recently, it was shown that IL-32 increases IFN-γ production by PBMCs. All 4 isoforms of IL32 have been shown to be active in multiple bioassays, and for the purposes of the invention any of the IL-32 isoforms, i.e. IL-32α, IL-32β, IL-32γ, IL-32δ or variants, derivatives, or fragments thereof may find use. The reference sequence for the human gene may be accessed at Genbank, number NG_029254.

The IL-32 protein contains a tyrosine sulfation site, 3 potential N-myristoylation sites, multiple putative phosphorylation sites, and an RGD cell-attachment sequence. Expression of this protein is increased after the activation of T-cells by mitogens or the activation of NK cells by IL-2. This protein induces the production of TNFα from macrophage cells. Alternate transcriptional splice variants, encoding different isoforms, have been characterized.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. All single letters used in the present invention to represent amino acids are used according to recognized amino acid symbols routinely used in the field.

For the purposes of the invention, a therapeutic form of IL-32 is the portion of the polypeptide that is sufficient to bind to its receptor and induce differentiation of monocytes to dendritic cells. Any of the known isoforms may be used, or a truncated version thereof that retains the biological activity of the native mature protein, e.g. truncated by from 1 to 100 amino acids at the C or N terminus. IL-32 variants useful in the present invention include one or more amino acid modifications within a native IL-32 protein, e.g., one or more amino acid modifications. According to the present invention, amino acid modifications include any naturally occurring or man-made amino acid modifications known or later discovered in the field. In some embodiments, amino acid modifications include any naturally occurring mutation, e.g., substitution, deletion, addition, insertion, etc. In some other embodiments, amino acid modifications include replacing existing amino acid with another amino acid, e.g., a conservative equivalent thereof. In yet some other embodiments, amino acid modifications include replacing one or more existing amino acids with non-natural amino acids or inserting one or more non-natural amino acids.

IL-32 variants also include various post-translation or post-expression modifications. For example, by employing the appropriate coding sequences, one may provide farnesylation or prenylation. In some embodiments, the IL-32 variants of the present invention can be PEGylated, where the polyethyleneoxy group provides for enhanced lifetime in the blood stream. The IL-32 variants of the present invention can also be combined with other proteins, such as the Fc of an IgG isotype, which can be complement binding, or with specific binding agents that allow targeting to specific moieties on a target cell.

In some embodiments, IL-32 variants of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some other embodiments, the second polypeptide is part or whole of Fc region. In some other embodiments, the second polypeptide is any suitable polypeptide that is substantially similar to Fc, e.g., providing increased size and/or additional binding or interaction with Ig molecules. In yet some other embodiments, the second polypeptide is part or whole of an albumin protein, e.g., a human serum albumin protein. In some other embodiments, the second polypeptide is useful for handling IL-32 variants, e.g., purification of IL-32 variants or for increasing its stability in vitro or in vivo. In yet some other embodiments, the second polypeptide is a marker sequence, such as a peptide which facilitates purification of the fused polypeptide.

IL-32 variants of the present invention can also include one or more modifications that do not alter primary sequences of the IL-32 variants of the present invention. For example, such modifications can include chemical derivatization of polypeptides, e.g., acetylation, amidation, carboxylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, IL-32 variants of the present invention include IL-32 variant having phosphorylated amino acid residues, e.g. phosphotyrosine, phosphoserine, or phosphothreonine.

In some other embodiments, IL-32 variants of the present invention include IL-32 variants further modified to improve their resistance to proteolytic degradation or to optimize solubility properties or to render them more suitable as a therapeutic agent. For example, IL-32 variants of the present invention further include analogs of a IL-32 variant containing residues other than naturally occurring L-amino acids, e.g. D-amino acids or non-naturally occurring synthetic amino acids. D-amino acids may be substituted for some or all of the amino acid residues.

According to the present invention, IL-32 variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Dendritic Cells and Uses Thereof

In the methods of the invention, dendritic cells are generated from precursor cells, usually monocytes, by contacting the precursor cells with an effective dose of IL-32. The precursor cells may be isolated from a suitable biological sample by methods known in the art, and may be isolated, or provided in a complex cell population. The cells may be contacted in vivo, or ex vivo. For ex vivo purposes the effective dose of IL-32 may be from about 0.1 ng/ml in culture medium, from about 0.5 ng/ml, from about 1 ng/ml, from about 5 ng/ml, from about 10 ng/ml. Utilization of a supra-optimal dose, as shown in the examples, is also effective, e.g. where the dose is about 200 ng/ml, about 500 ng/ml or more. Contacting may be from a period of time from about 6 hours, about 12 hours, about 24 hours, about 48 hours, or more. The cells may be maintained in ex vivo culture for 1, 2, 3, 4, 5, 6, 7, or more days.

Precursor cells can be obtained from lymphoid tissue, including bone marrow, blood, mobilized peripheral blood, spleen, lymph node, and cord blood. The precursors, e.g. monocytes, monocyte precursors, or complex populations comprising monocytes and/or monocyte precursors can be in a variety of developmental states such as stem cells, myeloid committed progenitors, monocytes, etc.

For in vivo purposes the dose may vary according to the route of delivery, patient size, condition, antigen, and the like, for example ranging from about 1 µg, 10 µg, 100 µg, 1 mg, 10 mg. 100 mg, or more. Administration may be targeted, e.g. to infected lesions, tumors, lungs, skin, etc., or maybe systemic, e.g. intramuscular, intravenous, intraperitoneal, intradermal, oral, etc. The administration may be combined with an antigen of interest, in a co-formulation or in separate, concurrent formulations. Administration of the IL-32 may be repeated as necessary, for example semi-daily, daily, semi-weekly, etc., for from 1, 2, 3, 4, 5, 6, or more administrations.

As used herein, dendritic cell (DC) refers to any member of a diverse population of morphologically similar cell types found in lymphoid or non-lymphoid tissues. DCs are referred to as "professional" antigen presenting cells, and have a high capacity for sensitizing MHC-restricted T cells. DCs may be recognized by function, by phenotype and/or by gene expression pattern, particularly by cell surface phenotype. These cells are characterized by their distinctive morphology, high levels of surface MHC-class II expression and ability to present antigen to $CD4^+$ and/or $CD8^+$ T cells, particularly to naïve T cells (Steinman et al. (1991) *Ann. Rev. Immunol.* 9:271; incorporated herein by reference for its description of such cells).

The cell surface of DCs is unusual, with characteristic veil-like projections, and is characterized by expression of the cell surface markers CD11c and MHC class II. Most DCs are negative for markers of other leukocyte lineages, including T cells, B cells, monocytes/macrophages, and granulocytes. Subpopulations of dendritic cells may also express additional markers including 33D1, CCR1, CCR2, CCR4, CCR5, CCR6, CCR7, CD1a-d, CD4, CD5, CD8alpha, CD9, CD11b, CD24, CD40, CD48, CD54, CD58, CD80, CD83, CD86, CD91, CD117, CD123 (IL3Rα), CD134, CD137, CD150, CD153, CD162, CXCR1, CXCR2, CXCR4, DCIR, DC-LAMP, DC-SIGN, DEC205, E-cadherin, Langerin, mannose receptor, MARCO, TLR2, TLR3 TLR4, TLR5, TLR6, TLR9, and several lectins. The patterns of expression of these cell surface markers may vary along with the maturity of the dendritic cells, their tissue of origin, and/or their species of origin.

Immature DCs express low levels of MHC class II, but are capable of endocytosing antigenic proteins and processing them for presentation in a complex with MHC class II molecules. Activated DCs express high levels of MHC class II, ICAM-1 and CD86, and are capable of stimulating the proliferation of naïve allogeneic T cells, e.g. in a mixed leukocyte reaction (MLR).

Functionally, DCs may be identified by any convenient assay for determination of antigen presentation. Such assays may include testing the ability to stimulate antigen-primed and/or naïve T cells by presentation of a test antigen, followed by determination of T cell proliferation, release of IL-2, and the like.

In certain embodiments of the invention, DCs of interest are autologous, meaning that they derived from the subject to be treated. In other embodiments, the DCs are from a donor (i.e., allogeneic). In certain of these embodiments, the allogeneic DCs are from a compatible donor, i.e., HLA typed so that they are histocompatible with the subject into which they will be transplanted.

In certain embodiments, DCs generated by the methods of the invention are enriched or isolated as is known in the art. In certain of these embodiments, DCs are enriched based on the cell surface expression of specific molecules (e.g., those noted above) using marker-specific monoclonal antibodies (e.g., sorting by flow cytometry, immunobead selection, immunopanning, etc.).

In certain embodiments, the DCs generated by the methods of the invention are frozen in liquid nitrogen (or equivalent) prior to use. If frozen, the cells may be stored in a 10% DMSO, 50% FCS, 40% RPMI 1640 medium in liquid nitrogen, or other suitable medium known in the art.

Dendritic cells of the invention have functional activities and phenotypes that are specifically associated with the maturity of the cell. Cell surface markers useful in the characterization of and classification of dendritic cells include: CD1, CD11a; CD11b; CD11c; F4/80; Fc.gamma. RII/III receptor (FcR); MHC class I; MHC class II; CD80; CD86; CD54; CD40; and CD117. Expression of CD1b is of particular interest.

Analyses of the cell surface using monoclonal antibodies are made using a flow cytometer, magnetic sorting, and the like. Briefly, the cells are either combined with monoclonal antibodies directly conjugated to fluorochromes, or with unconjugated primary antibody and subsequently with commercially available secondary antibodies conjugated to fluorochromes. The stained cells are analyzed using, for example, a flow cytometer (for example as available from Becton Dickinson, Mountain View, Calif.). Additional phenotypic characteristics of dendritic cells can be characterized by gene expression profiling e.g. by reverse-transcriptase polymerase chain reaction (RT-PCR).

DCs generated ex vivo by the methods of the invention are administered to a subject in any physiologically acceptable medium, normally intravascularly, although they may also be introduced into the targeted site, where the cells home to the site of inflammation. The number of cells administered may vary widely depending on the nature of the disease being treated and/or the antigen of interest. As such, the number of DCs administered can include at least about $1\times10^5$ DCs, at least about $1\times10^6$ DCs, at least about $1\times10^7$ DCs, at least about $1\times10^8$ DCs, at least about $1\times10^9$ DCs or more. In addition, the DCs can be administered in a single dose or at timed intervals.

In the methods of the invention, cells are transferred to a recipient in any physiologically acceptable excipient comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the route and device used for administration. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium.

An antigen of interest may be delivered along with the DCs, and may be given as a combined formulation, or as separate formulations. The antigen may be further provided in a booster dose, in combination with other adjuvants as known in the art, etc.

The activation and antigenic stimulation in the peripheral tissues activates the DC precursors to mature into functional DC, which are then able to take-up and process the antigen of interest. On maturation, the DC are competent to migrate to lymphatic organs, particularly T cell rich regions of the lymph nodes, where T cell activation occurs. Therefore, although the administration of antigen and activating agent is localized, the resulting immune response is not limited to that tissue.

Conditions of particular interest for use with the present methods involve a lack of T cell mediated response to antigen, for example chronic viral or bacterial infection, a lack of immune response to tumor antigens, and the like. In one aspect of the invention, the antigen is a tumor antigen, and is used to enhance the host immune response to tumor cells present in the body.

Antigens of interest include polypeptides and other immunogenic biomolecules, which may be isolated or derived from natural sources, produced by recombinant methods, etc., as known in the art. Alternatively complex antigens may be used, for example cell lysates, virus which may be inactivated, bacterial cells or fractions derived therefrom, and the like.

The dendritic cells of the invention are also useful when used in conjunction with vaccines such as, but not limited to, those for treating chronic bacterial infections, e.g. tuberculosis, leprosy, etc.; chronic viral infections such as those associated with herpesvirus, lentivirus and retrovirus, etc. Antigens of interest may also include allergens, e.g. for the conversion of a Th2 to a Th1 type response. The antigens which may be incorporated into the present formulations include viral, prokaryotic and eukaryotic antigens, including but not limited to antigens derived from bacteria, fungi, protozoans, parasites and tumor cells.

Potential tumor antigens for immunotherapy include tumor specific antigens, e.g. immunoglobulin idiotypes and T cell antigen receptors; oncogenes, such as p21/ras, p53, p210/bcr-abl fusion product; etc.; developmental antigens, e.g. MART- 1/Melan A; MAGE-1, MAGE-3; GAGE family; telomerase; etc.; viral antigens, e.g. human papilloma virus, Epstein Barr virus, etc.; tissue specific self-antigens, e.g. tyrosinase; gp100; prostatic acid phosphatase, prostate specific antigen, prostate specific membrane antigen; thyroglobulin, α-fetoprotein; etc.; and over-expressed self antigens, e.g. her-2/neu; carcinoembryonic antigen, muc-1, and the like.

As an alternative to injecting antigen, endogenous tissues expressing antigen can be used as an endogenous source of antigen. For example, tumors that express a tumor antigen maybe injected with the DCs to serve as the source of tumor antigen.

Antigenic formulations will typically contain from about 0.1 μg to 1000 μg, more preferably 1 μg to 100 μg, of the selected antigen. The antigen composition may additionally contain biological buffers, excipients, preservatives, and the like. The antigen is administered to the host in the manner conventional for the particular immunogen, generally as a single unit dose of an antigen in buffered saline, combined with the adjuvant formulation, where booster doses, typically one to several weeks later, may additionally be delivered enterally or parenterally, e.g., subcutaneously, intramuscularly, intradermally, intravenously, intraarterially, intraperitoneally, intranasally, orally, etc.

The subject cultured cells may also be used in a wide variety of ways, e.g. in gene discovery, the generation of dendritic cell subset-specific antibodies and probes; defining stages of dendritic cell differentiation and maturation; for induction of antigen specific responses in T and/or B lymphocytes; for dissection of antigen specific anergy or tolerance in T and/or B lymphocytes; for characterization of dendritic cell-natural killer cell interactions; for in vitro and in vivo analyses of dendritic cell-endothelial cell interactions; for screening assays, and for therapeutic purposes.

The cells of the present invention may also be used for screening biological response modifiers, i.e. compounds and factors that affect the various metabolic pathways of dendritic cells. For example, the subject cells may be used to screen for molecules that enhance or inhibit dendritic growth or differentiation or antigen presentation itself. Typically the candidate compound will be added to the dendritic cells, and the response of the dendritic cells monitored through evaluation of cell surface phenotype, functional activity such as ability to present antigen, patterns of gene expression, and the like. Of particular interest are screening assays for agents that have a low toxicity for human cells.

The term "agent" as used herein describes any molecule, e.g. protein or pharmaceutical, with the capability of altering the phenotype of a dendritic cell. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, including polypeptides, nucleic acids, and small organic compounds, e.g. having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In addition, the cells of the present invention may be used to generate antibodies for cell-specific proteins. For example, antibodies to cell-surface markers may be generated and used to purify a subpopulation from a heterogenous population of cells using a cell sorting system. Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation. Phage display is particularly useful for poorly immunogenic cell surface molecules and can be conducted using subtraction-based approaches to preferentially select for molecules expressed by, for example, either activated or tolerogenic dendritic cells.

Because dendritic cells can take up, process and present exogenous antigen (including proteins, glycoproteins and peptides), these cells are valuable tools that can be used to identify dominant epitopes of a particular antigen. Dendritic cells naturally process and present exogenous protein, permitting epitope mapping studies that better mimic the in vivo process.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

It has been unclear whether the ability of the innate immune system to recognize distinct ligands from a single microbial pathogen via multiple pattern recognition receptors (PRRs) triggers common pathways, or differentially triggers specific host responses. In the human mycobacterial infection leprosy, we found that activation of monocytes via nucleotide-binding oligomerization domain-containing protein 2 (NOD2) by its ligand muramyl dipeptide, as compared to activation via heterodimeric Toll-like receptor 2 and Toll-like receptor 1 (TLR2/1) by triacylated lipopeptide, preferentially induced differentiation into dendritic cells (DCs), which was dependent on a previously unknown interleukin-32 (IL-32)-dependent mechanism. Notably, IL-32 was sufficient to induce monocytes to rapidly differentiate into DCs, which were more efficient than granulocyte-macrophage colony-stimulating factor (GM-CSF)-derived DCs in presenting antigen to major histocompatibility complex (MHC) class I-restricted CD8+ T cells. Expression of NOD2 and IL-32 and the frequency of CD1b+ DCs at the site of leprosy infection correlated with the clinical presentation; they were greater in patients with limited as compared to progressive disease. The addition of recombinant IL-32 restored NOD2-induced DC differentiation in patients with the progressive form of leprosy. In conclusion, the NOD2 ligand-induced, IL-32-dependent DC differentiation pathway contributes a key and specific mechanism for host defense against microbial infection in humans.

The ability of the innate immune response to combat infection involves germline-encoded PRRs, which detect evolutionarily conserved pathogen-associated molecular patterns (PAMPs) of the microbial invader. PRRs are located in different subcellular compartments, including at the cell surface, in the cytoplasm and within endosomes. Some pathogens contain several PAMPs that activate distinct PRRs; however, many studies have indicated that these PAMP-PRR complexes trigger overlapping immune programs. Key functions of the innate immune response include direct phagocytic and antimicrobial activity against the pathogen by macrophages and the instruction of the adaptive T cell response by DCs. We hypothesized that distinct PAMPs through activation of their respective PRRs might differentially activate the pathways by which monocytes differentiate into macrophages and DCs to regulate the host response against microbial infection.

Leprosy, caused by the intracellular pathogen *Mycobacterium leprae*, offers an attractive model to investigate innate immune responses to infection. The disease not only is a major health and economic burden in developing countries but also presents as a spectrum in which the clinical manifestations correlate with the type of immune response to the pathogen. At one end of the disease spectrum, patients with tuberculoid leprosy (T-lep) show the resistant response that restricts the growth of the pathogen. At the opposite end of this spectrum, patients with lepromatous leprosy (L-lep) show susceptibility to disseminated infection. These clinical presentations correlate with the type of acquired T cell-mediated immunity against *M. leprae*, including T helper type 1 (TH1) cytokines, which are present in T-lep lesions and diminished in L-lep lesions. Conversely, antibody responses and TH2 cytokines are more prevalent in lesions from patients with L-lep. The frequency of DCs at the site of disease correlates with the clinical form of the disease, as it is higher in T-lep than in L-lep lesions, providing further rationale for investigating mechanisms of macrophage and DC differentiation by individual PAMPs and PRRs.

The innate immune response to mycobacterial infection has been shown to involve both TLRs and NOD-like receptors (NLRs). TLR2/1 is a cell surface heterodimer that detects mycobacterial lipoproteins and requires a triacyl group for its activity. The distribution of TLR2 and TLR1 in leprosy lesions correlates with host resistance to the pathogen, and polymorphisms in the TLR2 and TLR1 genes have been associated with leprosy and its spectrum of immune reactions.

NOD2 is a cytoplasmic receptor belonging to the NOD-like receptor family. NOD2 recognizes muramyl dipeptide (MDP), part of the peptidoglycan of the mycobacterial cell wall. NOD2 polymorphisms are associated with susceptibility to leprosy. Together, NOD2 and TLR2 activation act synergistically to induce monocyte cytokine responses$_3$, suggesting that they promote overlapping pathways in innate immunity. In the present study, found that activation of specific PRRs, NOD2 or TLR2/1, triggers induction of distinct innate immune responses, in particular macrophage and DC differentiation pathways, in leprosy.

RESULTS

Figure 7:
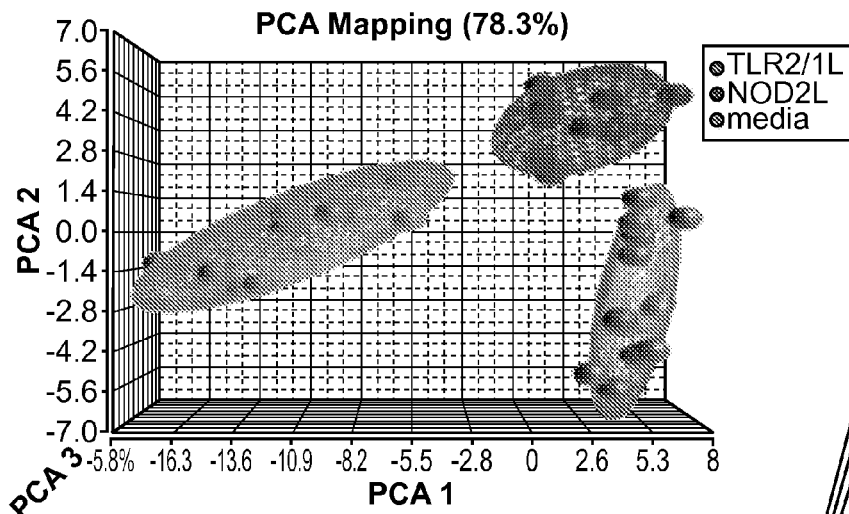
FIG. 7. Principle component analysis (PCA). PCA using differentially expressed genes between NOD2L, TLR2/1L and media (two-fold, P<0.05) demonstrates three separate spheres for media, NOD2L or TLR2/1L activated monocytes (n=5, 6 h, 24 h).
Figure 8:
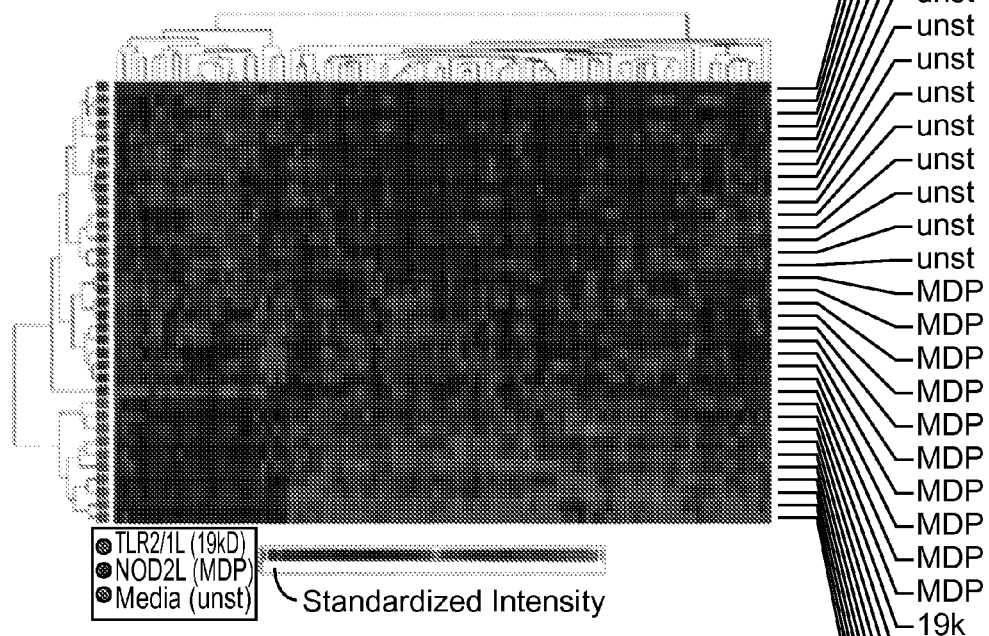
FIG. 8. Cluster Map. Cluster map constructed using differentially expressed genes between media, NOD2L and TLR2/1L (two-fold, P<0.05) demonstrates three separate clusters for media, NOD2L or TLR2/1L activated monocytes (n=5, 6 h, 24 h).

Identification of NOD2- and TLR2/1-induced functional pathways. To determine the specific and shared immune responses triggered by distinct PRRs recognizing a microbial pathogen, we activated human peripheral blood monocytes from five healthy donors with two defined mycobacterial ligands: MDP, which activates cytoplasmic NOD2 (NOD2 ligand, NOD2L) and the mycobacterial 19-kDa triacylated lipopeptide, which activates cell surface TLR2/1 (TLR2/1 ligand, TLR2/1 L). The concentration of NOD2L (1 µg ml$^{-1}$) and TLR2/1L (1 µg ml$^{-1}$) used for these studies was determined by dose titration of the ligands, initially measuring IL-12 p40 release and defensin β4 mRNA as the immunologic readout. To identify molecular pathways induced by these different ligands, we collected cells at 0, 6 and 24 h and isolated mRNAs to obtain gene expression profiles using Affymetrix microarrays. Genes with differential expression between the two stimuli were identified by fold change and Student's t test P value thresholds (FIGS. 7 and 8).

Figure 9:
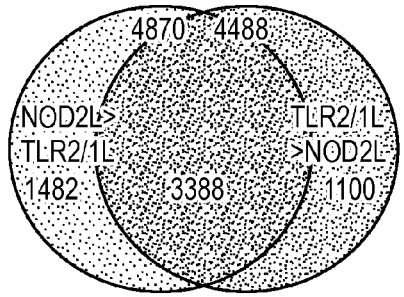
FIG. 9. Venn diagram. The number of genes induced by NOD2L and/or TLR2/1L greater than 1.5-fold compared to media is indicated. Genes induced by both, NOD2L and TLR2/1L appear purple. (n=5, P<0.05).

We defined four main classes of genes on the basis of comparisons between activated monocytes and control samples grown in medium: (i) all genes induced by NOD2L versus medium control (NOD2L>medium, 1.5-fold, P<0.05), (ii) all genes induced by TLR2/1L versus medium control (TLR2L>medium, 1.5-fold, P<0.05), (iii) genes that were induced only by NOD2L but not by TLR2/1L (NOD2L>TLR2L: NOD2L/medium>1.5 and TLR2/1L/medium<1.5) and (iv) genes that were induced only by TLR2/1L but not by NOD2L (TLR2L>NOD2L: TLR2/1L/medium>1.5 and NOD2L/medium<1.5). There were 3,388 common gene probes induced by NOD2L and TLR2/1L. NOD2L and TLR2/1L also activated distinct gene sets, 1,482 genes specifically by NOD2L and 1,100 specifically by TLR2/1L (FIG. 9).

Figure 1C:
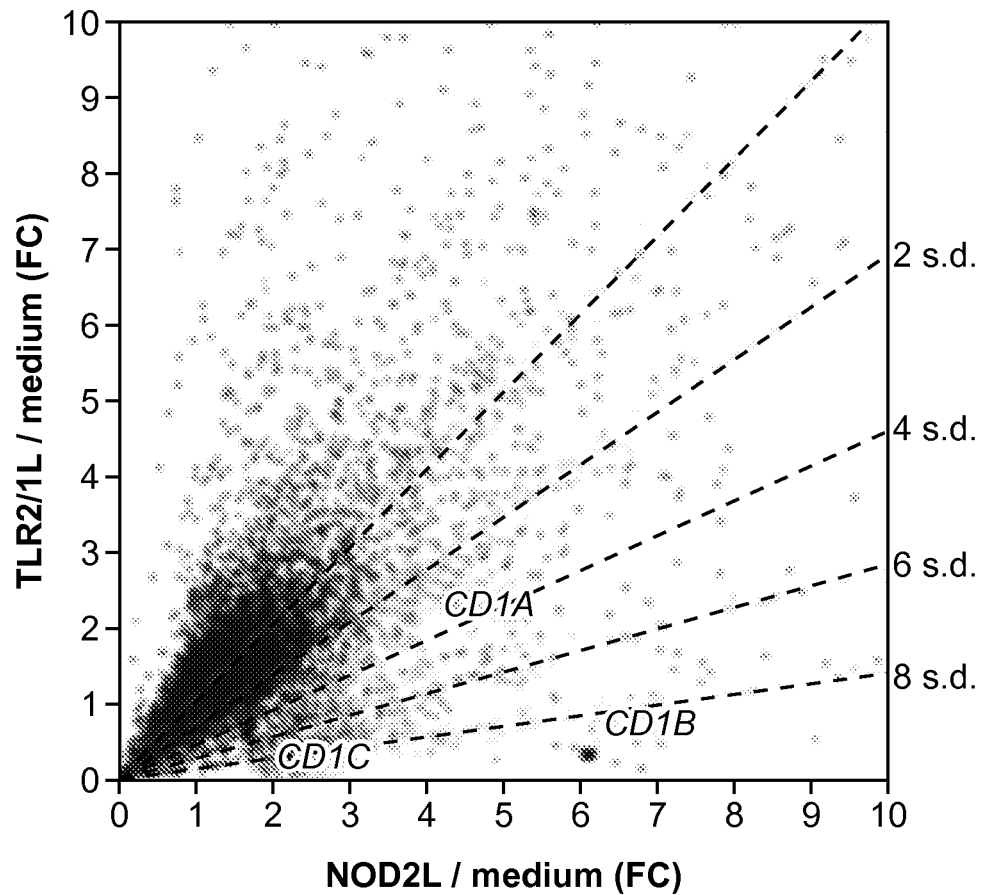

We performed enrichment analysis using Ingenuity pathways analysis (IPA) of the gene expression data to identify the main canonical pathways associated with the NOD2L- and TLR2/1L-induced gene sets. The genes induced in monocytes were evaluated according to their statistical association with each of 340 canonical pathways. For the gene sets induced by NOD2L but not TLR2/1L, the DC-related lipid antigen presentation by CD1 pathway showed the fourth highest statistical association of the 340 canonical pathways (FIG. 1a; Benjamini-Hochberg corrected P value=0.05). Furthermore, for the gene set induced by NOD2L versus medium, the DC-specific maturation pathway showed the third strongest association of the 340 canonical pathways (FIG. 1a). The association of NOD2L-induced genes with canonical pathways specific for DC function prompted a comparison of all four listed canonical DC pathways in the Ingenuity database. Both the lipid antigen presentation by CD1 and antigen presentation pathways were specifically associated with the NOD2L-induced gene sets as compared to the TLR2/1L-induced gene sets. In contrast, the two other canonical DC pathways, DC maturation and DC crosstalk, were significantly associated with both NOD2 and TLR2/1 activation (FIG. 1b). The lipid antigen presentation by CD1 pathway includes the group I CD1 antigen presentation molecules CD1A, CD1B, and CD1C, all preferentially upregulated by TLR2/1L activation of monocytes, with the ratio of NOD2L versus TLR2/1L induction being more than 2 s.d. from the mean for each (FIG. 1c).

Figure 10:
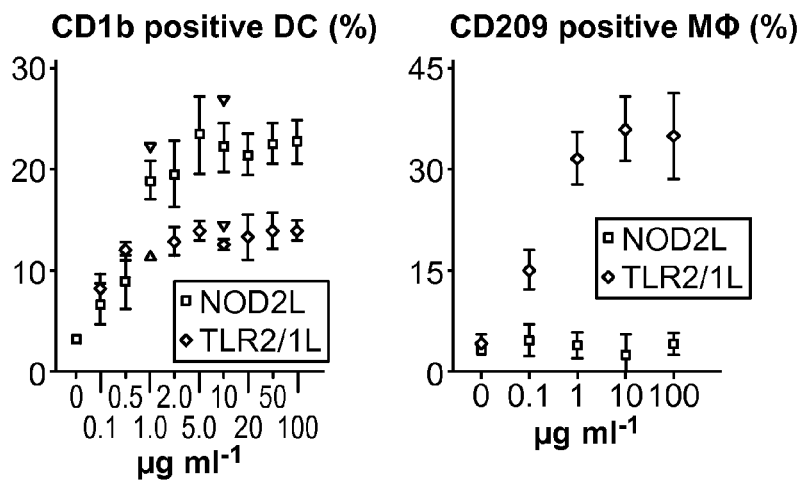
FIG. 10. Dose titration of NOD2L and TLR2/1L for induction of DC and Mϕ. Purified human monocytes were activated with either NOD2L or TLR2/1L at various concentrations (μg ml$^{-1}$) for 48 hours and analyzed by flow cytometry for the expression of CD1b (DC) and CD209 (Mø). Data are shown as mean+/−SEM, n≥4. Statistical significance was calculated by two-tailed Students t-test and showed significant higher induction of CD1b$^+$ DC by NOD2L at doses ≥1 μg ml$^{-1}$ and significant higher percentage of CD209$^+$ Mø induced by TLR2/1L at doses ≥0.1 μg ml$^{-1}$.
Figure 11:
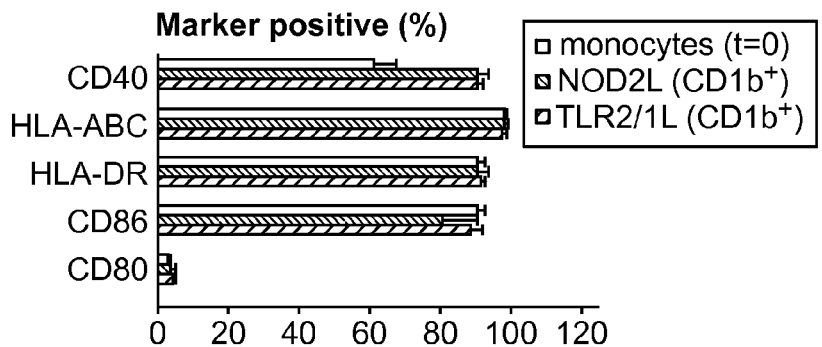
FIG. 11. Expression of key markers involved in antigen presentation in NOD2L-vs TLR2/1L induced CD1b$^+$ DC. Purified human monocytes were activated with either NOD2L (1 μg ml$^{-1}$) or TLR2/1L (1 μg ml$^{-1}$) for 48 hours. Surface expression of markers involved in antigen presentation was assessed by flow cytometry, gated on CD1b$^+$ DC induced by either NOD2L or TLR2/1L; data are indicated as mean percentage positive, +/−SEM, n=6. Two-tailed Students t test showed no statistical significant differences in the percentage positive cells between the different ligands.
Figure 12:
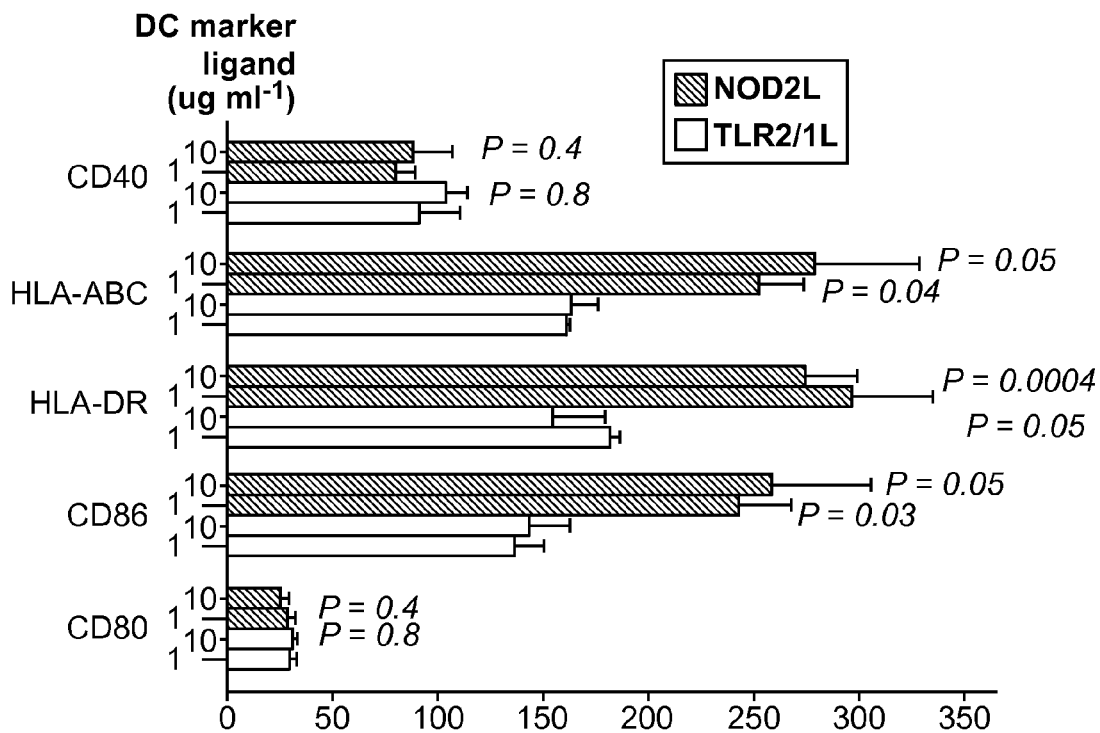
FIG. 12. Phenotypic differences between the NOD2L- and TLR2/1L-induced DC at optimal and supraoptimal conditions. Surface expression of markers involved in antigen presentation was assessed by flow cytometry, gated on CD1b$^+$ DC. Induction of DC was performed at optimal and supraoptimal doses of NOD2L (1 μg ml$^{-1}$, 10 μg ml$^{-1}$) or TLR2/1L (1 μg ml$^{-1}$, 10 μg ml$^{-1}$); data are indicated as mean MFI+/−SEM, n=6. Statistical significance was calculated by paired two-tailed Students t-test.

Activation of monocytes by NOD2L induces CD1b$^+$ DCs. Given that TLR2/1L induces both CD1b$^+$ DCs and CD209$^+$ macrophages and our bioinformatics finding that NOD2 preferentially triggers DC functional pathways, we compared the capacity of NOD2 versus TLR2/1 activation to trigger DC and macrophage differentiation. We activated peripheral blood monocytes with either TLR2/1L or NOD2L for 48 h and, subsequently, measured CD1b$^+$ and CD209$^+$ cells by flow cytometry. Although CD209 is expressed on DCs derived by treatment of monocytes with GM-CSF plus IL-4, it is not expressed on DCs derived by GM-CSF treatment alone. CD209 is expressed on macrophages, not DCs, in a variety of human tissues and diseases. In addition, TLR2/1-induced CD209$^+$ cells were previously shown to express macrophage but not DC markers. Because low levels of CD1b are induced in monocytes cultured in medium containing 10% human serum, we performed additional experiments using fetal calf serum, with which there is minimal background induction of CD1b24. The frequency of CD1b$^+$ DCs was twofold greater from NOD2L versus TLR2/1L activation (FIG. 2a,b), whereas CD209$^+$ macrophages were induced only by TLR2/1L (FIG. 2a,b) across a wide range of ligand concentrations (FIG. 10). The expression of CD1a and CD1c was also greater on NOD2L-versus TLR2/1L-activated monocytes, consistent with the microarray results. The percentages of CD40$^+$, human leukocyte antigen-ABC$^+$ (HLA-ABC$^+$), HLA-DR$^+$, CD86$^+$ and CD80$^+$ cells were similar (FIG. 11). However, the mean fluorescence intensities (MFIs) of HLA-ABC, HLA-DR and CD86 were significantly greater on the NOD2L-versus the TLR2/1L-induced CD1b$^+$ cells, as well as on resting monocytes (FIG. 2c), and they were consistent when comparing two different doses of each ligand (FIG. 12).

To compare the functional capacity of NOD2L-versus TLR2/1L-differentiated CD1b$^+$ DCs, we performed standard MHC class I and MHC class II antigen presentation assays. NOD2L- and TLR2/1L-induced CD1b$^+$ DCs were generated and then isolated by immunomagnetic sorting with CD1b-specific monoclonal antibody (mAb).

Figure 2:
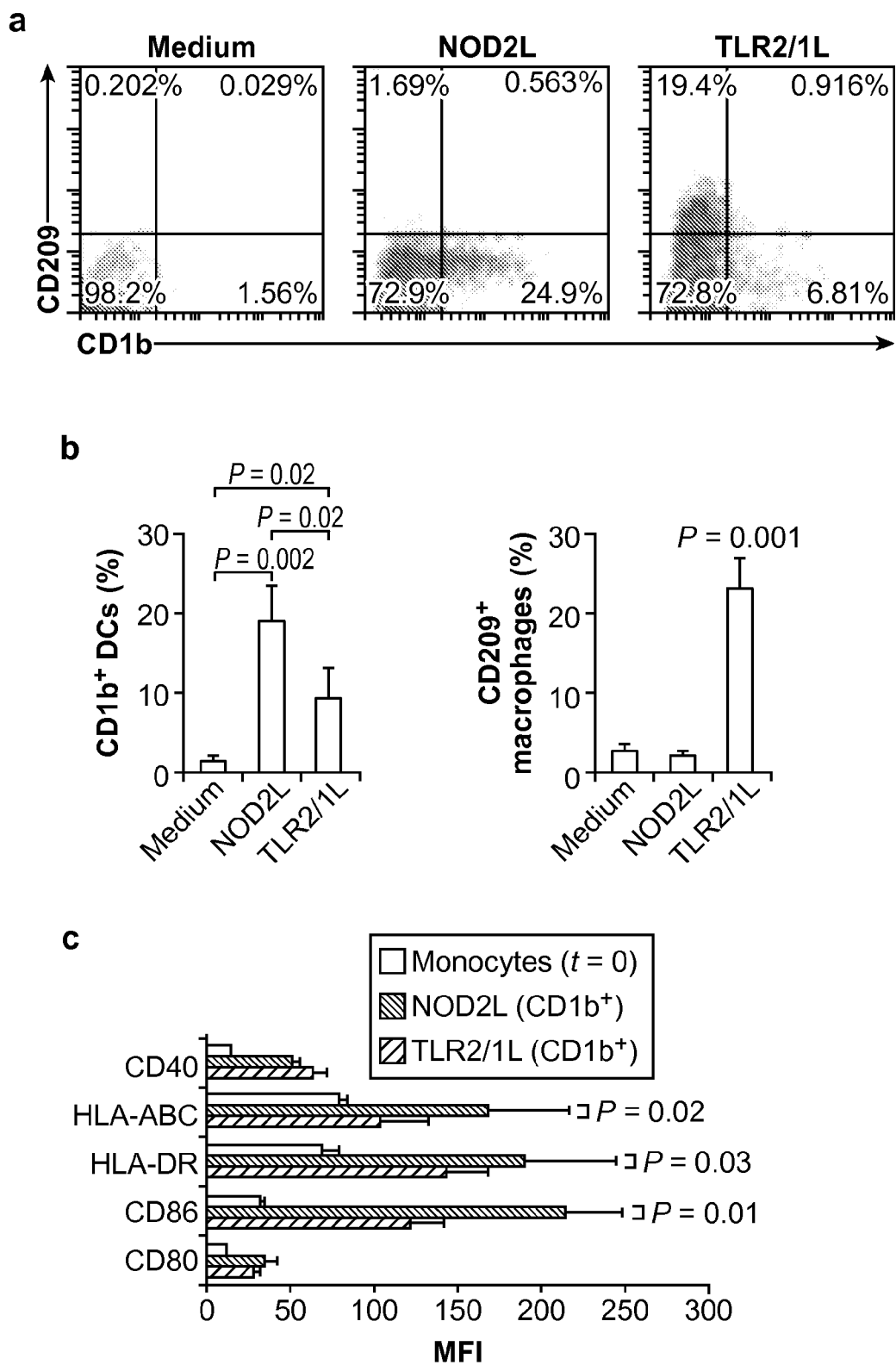
FIG. 2. NOD2L is a potent inducer of functional CD1b$^+$ DCs. Purified human monocytes activated with either NOD2L (1 µg ml$^{-1}$) or TLR2/1L (1 µg ml$^{-1}$) for 48 h analyzed by flow cytometry for the expression of CD1b (DCs) and CD209 (macrophages). (a) Representative flow cytometric analyses with double labeling for CD1b and CD209, shown for each condition. (b) CD1b and CD209 expression, shown as mean percentage positive ±s.e.m., n=8. (c) Surface expression of markers involved in antigen presentation by flow cytometry, gated on CD1b$^+$ DCs induced by either NOD2L (1 μg ml$^{-1}$) or TLR2/1 L (1 μg ml$^{-1}$); data are indicated as mean MFI±s.e.m., n=6. (d-f) T cell response using NOD2L- or TLR2/1L-induced purified CD1b$^+$ DCs in the context of tetanus toxoid and autologous CD8+ T cells (d) as well as various concentrations of *M. leprae* GroES protein (e) or GroES peptide and an MHC class II-restricted CD4+ T cell clone BCD4.9 (f). Proliferation shown as $^3$H-thymidine incorporation and IFN-γ secretion. Data are representative of triplicate wells of three independent experiments ±s.e.m. Statistical significance was calculated by two-tailed Student's t test. AU, arbitrary units.
Figure 2:
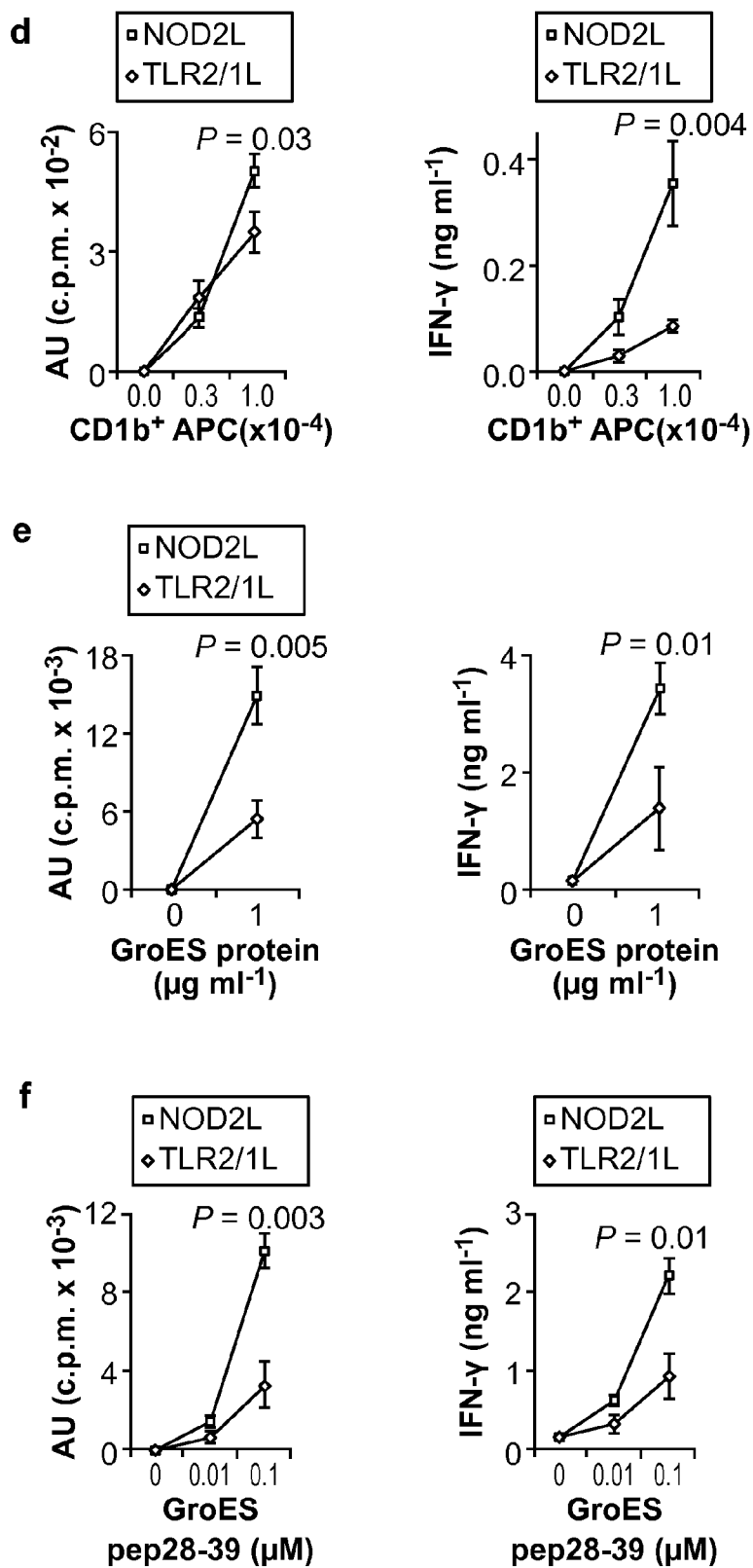
Figure 13:
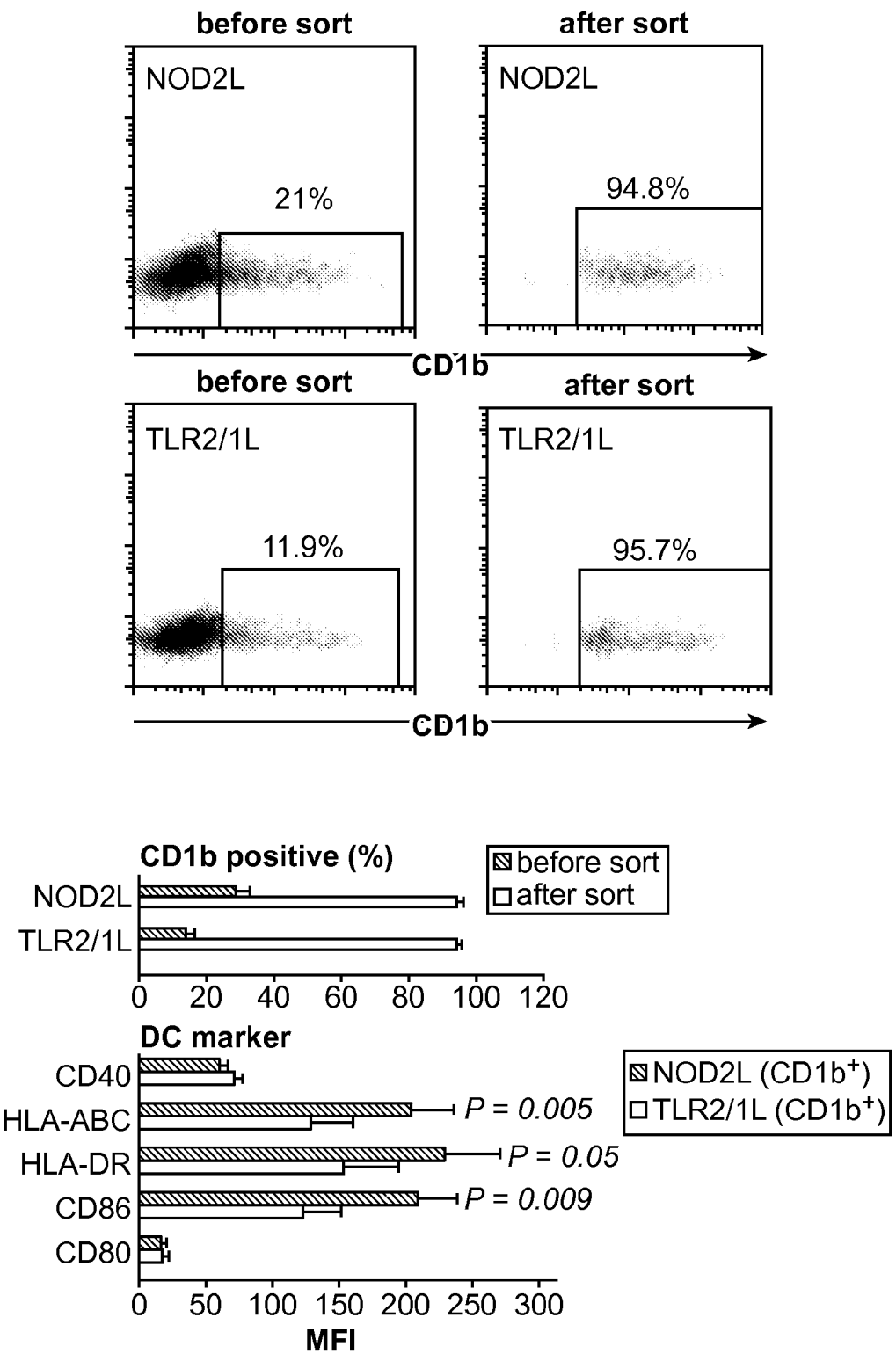
FIG. 13. Phenotypic characterization of purified NOD2L- and TLR2/1L-induced DC.

The sorted cells were ≥95% CD1b$^+$ and reflected the phenotypic pattern of unsorted CD1b$^+$ cells (FIG. 13). NOD2L-induced CD1b$^+$ DCs were more potent antigen-presenting cells than TLR2/1L-induced CD1b$^+$ DCs in terms of presentation of tetanus toxoid to CD8$^+$ T cells, as assessed by both 3H-thymidine incorporation and interferon-γ (IFN-γ) production (FIG. 2d). These differences were consistent at a tenfold higher concentration of each ligand (FIG. 14). The potential of these immature DCs to present and process antigen via MHC class II was assessed using a CD4$^+$ T cell clone (BCD4.9) that recognizes the *M. leprae* GroES protein and a defined peptide spanning amino acids 28-39 in an HLA-DR15-restricted manner. We isolated NOD2L- and TLR2/1L-induced CD1b+ DCs from an HLA-DR15-matched healthy donor by immunomagnetic selection. NOD2L-induced CD1b$^+$ DCs were more potent antigen-presenting cells than TLR2/1L-induced CD1b$^+$ DCs, in terms of processing and presentation of *M. leprae* GroES protein and the specific *M. leprae* GroES peptide to the T cell clone (FIG. 2e,f).

Figure 3:
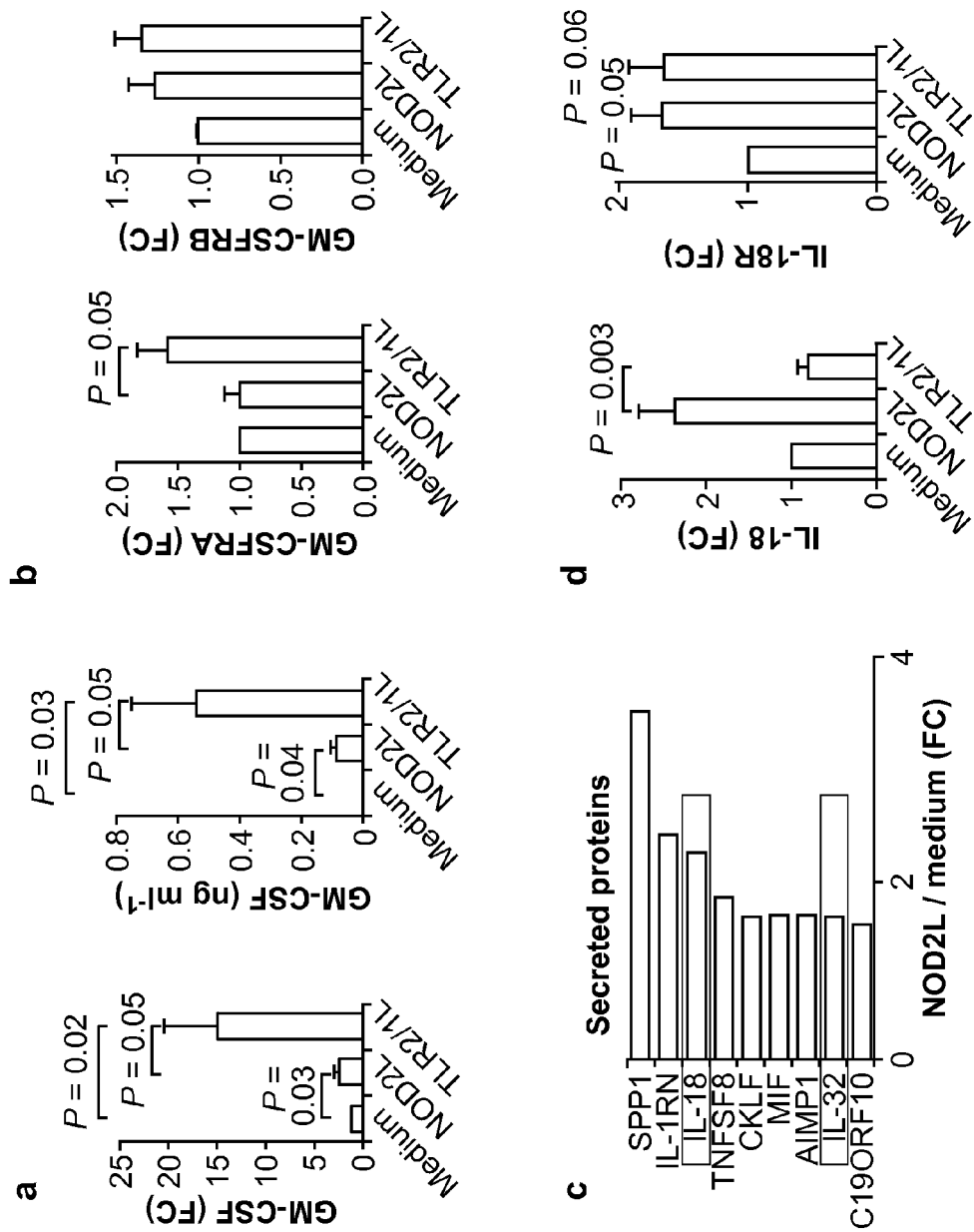
FIG. 3. NOD2L induces an IL-32-dependent DC program. (a,b) Induction of GM-CSF mRNA and protein (a) and GM-CSF receptor (GM-CSFRA, GM-CSFRB) (b) by NOD2L (1 μg ml$^{-1}$) and TLR2/1L (1 μg ml$^{-1}$) in human monocytes, mean±s.e.m., n=5. (c) Gene expression profile data analysis for genes coding for secreted molecules that were enhanced by NOD2L but not TLR2/1 L (NOD2L>TLR2/1L). SPP1, secreted phosphoprotein 1; IL-1 RN, IL-1 receptor antagonist; TNFSF8, tumor necrosis factor (ligand) superfamily, member 8; CKLF, chemokine-like factor 1; MIF, macrophage migration inhibitory factor; AIMP1, aminoacyl tRNA synthetase complex-interacting multifunctional protein 1; C19ORF10, chromosome 19 open reading frame 10. (d,e) Induction of IL-18 and IL-18R mRNA and IL-32 mRNA and protein by NOD2L (1 μg ml$^{-1}$) versus TLR2/1 L (1 μg ml$^{-1}$), data represent mean±s.e.m., n=5. (f,g) Induction of IL-32 mRNA by TLR and NLR ligands and live *M. leprae* at various multiplicities of infection. (h) Effect of siIL32 knockdown on NOD2L induction of IL-32 mRNA and induction of CD1b$^+$ DCs. AU, arbitrary units. Data are represented as mean±s.e.m., n=4. Statistical significance was calculated by two-tailed Student's t test.
Figure 3:
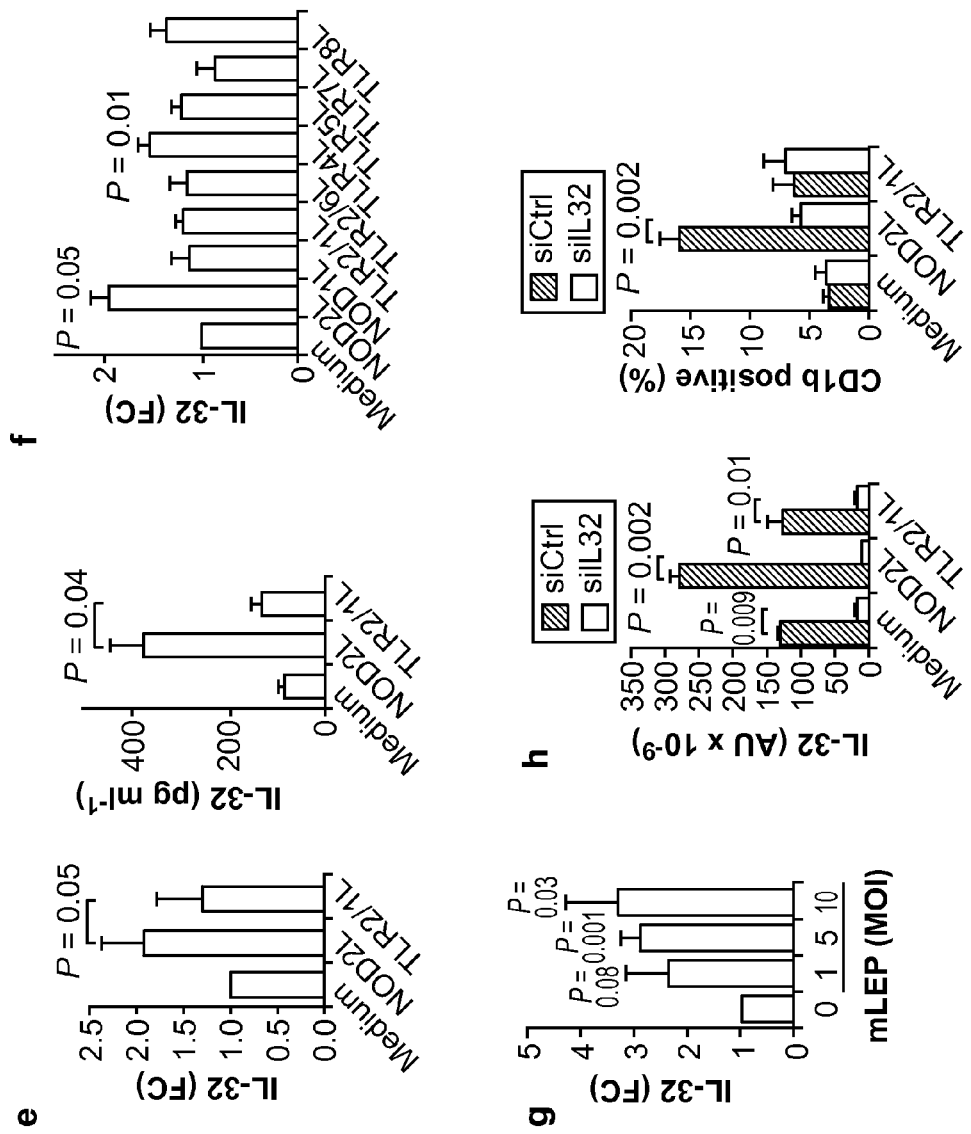

The mechanism of NOD2L-induced DC differentiation. Given that GM-CSF is known to be a potent inducer of DC differentiation, we investigated the differential ability of NOD2L versus TLR2/1L to induce expression of GM-CSF and its receptor. TLR2/1 activation of monocytes induced GM-CSF mRNA and protein (FIG. 3a) and the GM-CSF receptor α chain GM-CSFRA mRNA (FIG. 3b) more strongly than did NOD2L activation. The GM-CSF receptor β chain GM-CSFRB mRNA was equally upregulated by both ligands (FIG. 3b). TLR2/1L-induced DC differentiation was completely and significantly (P=0.01) (FIG. 15) blocked by the addition of neutralizing GM-CSF-specific mAbs, as previously reported. In contrast, NOD2L-induced DC differentiation was only partially blocked by neutralization of GM-CSF and was not significantly different compared to isotype control-treated cells (FIG. 15). Therefore, the mechanism by which NOD2L, as compared to TLR2/1L, more potently induces monocytes to differentiate into DCs does not seem to be related to GM-CSF release or receptor expression.

To determine the mechanism by which NOD2L induces DC differentiation, we performed IPA to identify transcripts encoding secreted proteins differentially induced in NOD2L-versus TLR2/1L-activated monocytes. We found nine candidate genes to be induced more by NOD2L than by TLR2/1L and classified to encode secreted proteins in activated monocytes (FIG. 3c). Further analysis of these candidate genes indicated that one gene, IL32, encodes a secreted protein reported to have direct action on monocytes leading to the induction of proinflammatory cytokines including tumor necrosis factor-α, IL-1β, IL-6, IL-8 and chemokines. Furthermore, two of the candidate genes, IL18 and IL32, encode secreted proteins that are part of a common pathway reported to be involved in the host response to mycobacteria. IL-32 has been shown to contribute to the pathogenesis of several infectious, autoimmune$_{31}$ and immunoregulatory disorders, including inflammatory bowel disease$_{32}$ and cancer. The human IL-32 receptor has not been identified, and no rodent orthologs of IL-32 have been reported.

IL-18 mRNA was induced greater than twofold after NOD2L activation of monocytes but not induced by TLR2/1L, whereas IL-18R mRNA was induced equally by both NOD2L and TLR2/1L (FIG. 3d). Additionally, IL-32 was more strongly induced in monocytes treated with NOD2L as compared to TLR2/1L, both at the mRNA and the protein levels (FIG. 3e). IL-32 mRNA was significantly induced in monocytes by NOD2L and TLR4L but not by other ligands (FIG. 3f). Finally, infection of monocytes with live *M. leprae* at increasing multiplicities of infection induced IL-32 mRNA (FIG. 3g).

Next, we investigated the requirement for IL-32 in NOD2L-induced DC differentiation using siRNA knockdown. Transfection of siRNA targeting IL-32 mRNA (silL32) into primary human monocytes knocked down IL-32 mRNA by >90% in cultures containing medium, NOD2L and TLR2/1L (FIG. 3h). The ability of NOD2L to induce CD1b expression was blocked by >80% by silL32, whereas, in contrast, the ability of TLR2/1L to induce CD1b expression, although at a lower level of induction, was not affected by silL32 (FIG. 3h). Knockdown of IL-32 mRNA did not directly affect NOD2L-induced IL-6, IL-8 and IL-10 mRNA levels (FIG. 16) but blocked induction of IL-32 and of CD1b$^+$ DCs (FIG. 17). NOD2L induction of CD1b expression was partially blocked by IL-18-specific mAb (FIG. 18). These data indicate that IL-32 production is required for NOD2L- but not TLR2/1L-induced CD1b$^+$ DC differentiation.

We next investigated whether IL-18 and IL-32 are sufficient to induce monocytes to differentiate into DCs. The addition of recombinant IL-32 to primary monocytes induced CD1b expression in a dose-dependent manner (FIG. 4a); however, IL-18 did not induce CD1b expression (FIG. 19). IL-32-differentiated cells had a dendritic morphology similar to that of NOD2L- and GM-CSF-differentiated cells (FIG. 20) and expressed CD1b whether cultured with 10% FCS or serum-free medium (FIG. 21).

Figure 4:
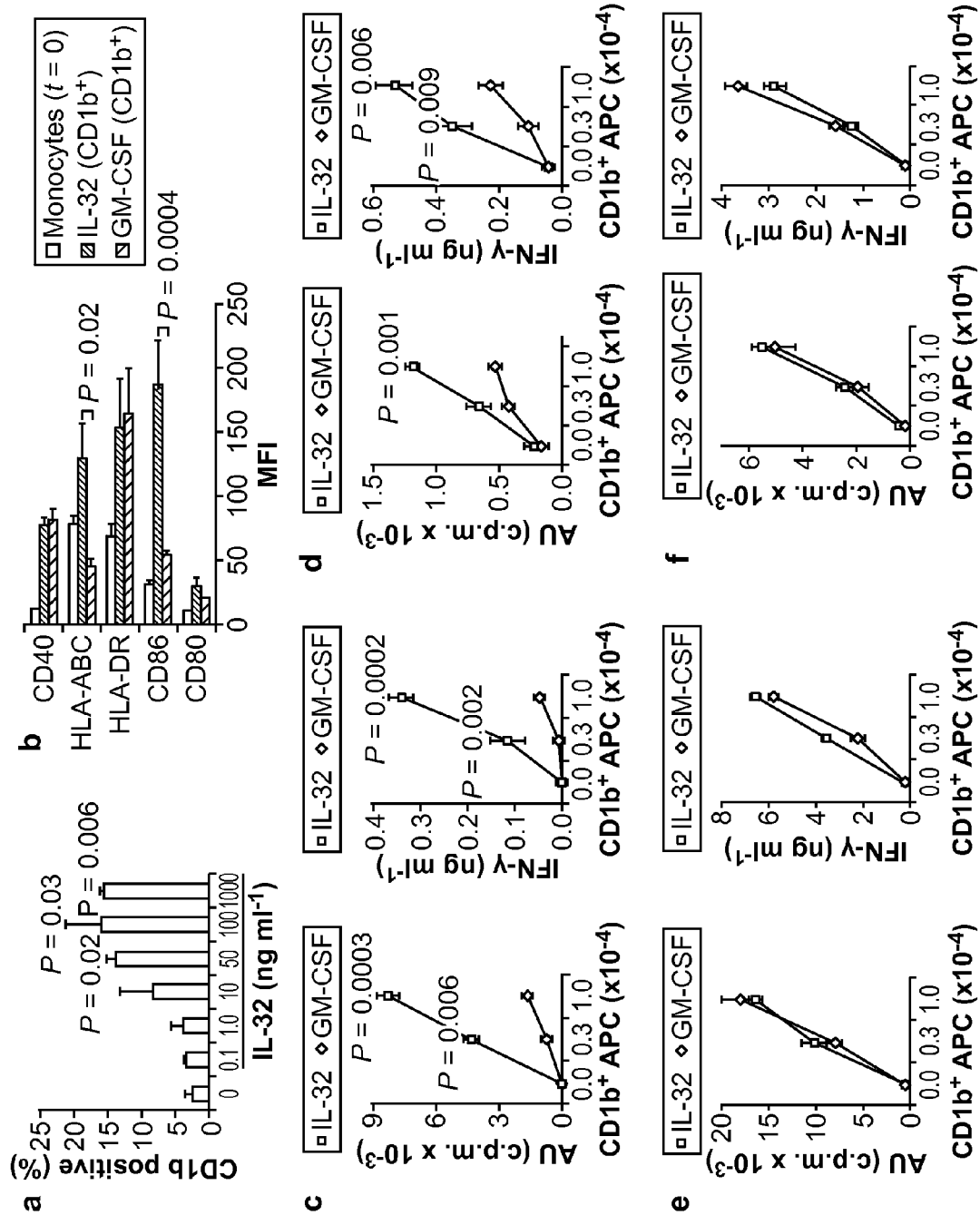
FIG. 4. IL-32-induced DCs are potent antigen-presenting cells for MHC class I-restricted antigens. (a) Ability of recombinant IL-32 to induce CD1b$^+$ DCs. (b) Surface expression of markers involved in antigen presentation, gated on CD1b$^+$ DCs induced by either recombinant IL-32 (50 ng ml−1) or recombinant GM-CSF (1 U ml$^{-1}$); data are indicated as mean±s.e.m., n=6. (c-f) Ability of IL-32-(50 ng ml$^{-1}$) or GM-CSF-(1 U ml$^{-1}$) derived CD1b$^+$ DCs to stimulate a T cell response in the context of tetanus toxoid (c), influenza peptide M1 with autologous CD8$^+$ T cells (d), *M. leprae* GroES protein (e) or GroES peptide with the MHC class II-restricted T cell clone BCD4.9. (f) Proliferation shown as $^3$H-thymidine incorporation and IFN-γ secretion. Data are shown as mean of triplicate wells of at least two independent experiments, ±s.e.m. Statistical significance was calculated by two-tailed Student's t test.

As both IL-32 and GM-CSF induce DC differentiation, we compared the phenotype and antigen presentation function of these two types of DCs. GM-CSF-derived DCs without the addition of IL-4 are immature DCs that more closely resemble circulating and tissue DCs by cell surface phenotype. Dose titration experiments revealed that treatment of monocytes with GM-CSF induced a greater percentage of CD1b$^+$ cells as compared to treatment with IL-32 (FIG. 22). The effect of the cytokines at optimal and supraoptimal doses indicated that both IL-32- and GM-CSF-derived CD1b$^+$ DCs expressed similar percentages of the other DC markers (FIG. 23). However the MFIs of HLA-ABC and CD86 were significantly higher on IL-32-derived versus GM-CSF-derived CD1b$^+$ DCs (FIG. 4b and FIGS. 24 and 25).

Given the differential expression of MHC class I on IL-32-versus GM-CSF-derived DCs, we investigated the potential of the different DCs to present antigen. We found IL-32-derived DCs to be more potent than GM-CSF-derived DCs in presenting tetanus toxoid and influenza peptide M1 to CD8$^+$ T cells in terms of proliferation and IFN-γ release (FIG. 4c,d and FIG. 26). We also verified the potency of IL-32-derived DCs in stimulating MHC class I-restricted T cell responses by tetramer labeling, using HLA-A*0201-influenza-M1 (GILG-FVFTL) tetramers (FIG. 27). Although IL-32-induced DCs were more potent than GM-CSF-induced DCs in presentation of antigen via MHC class I to CD8+ T cells, both IL-32- and GM-CSF-induced DCs were equally effective in presenting the *M. leprae* GroES protein and peptide via MHC class II to CD4+ T cells (FIG. 4e,f). This was consistent with the demonstration that MHC class I expression was higher on IL-32-versus GM-CSF-derived DCs, whereas MHC class II expression was equivalent (FIG. 4b). Together, these data indicate that IL-32 is sufficient to induce the differentiation of DCs with potent MHC class I antigen-presenting function.

Figure 5:
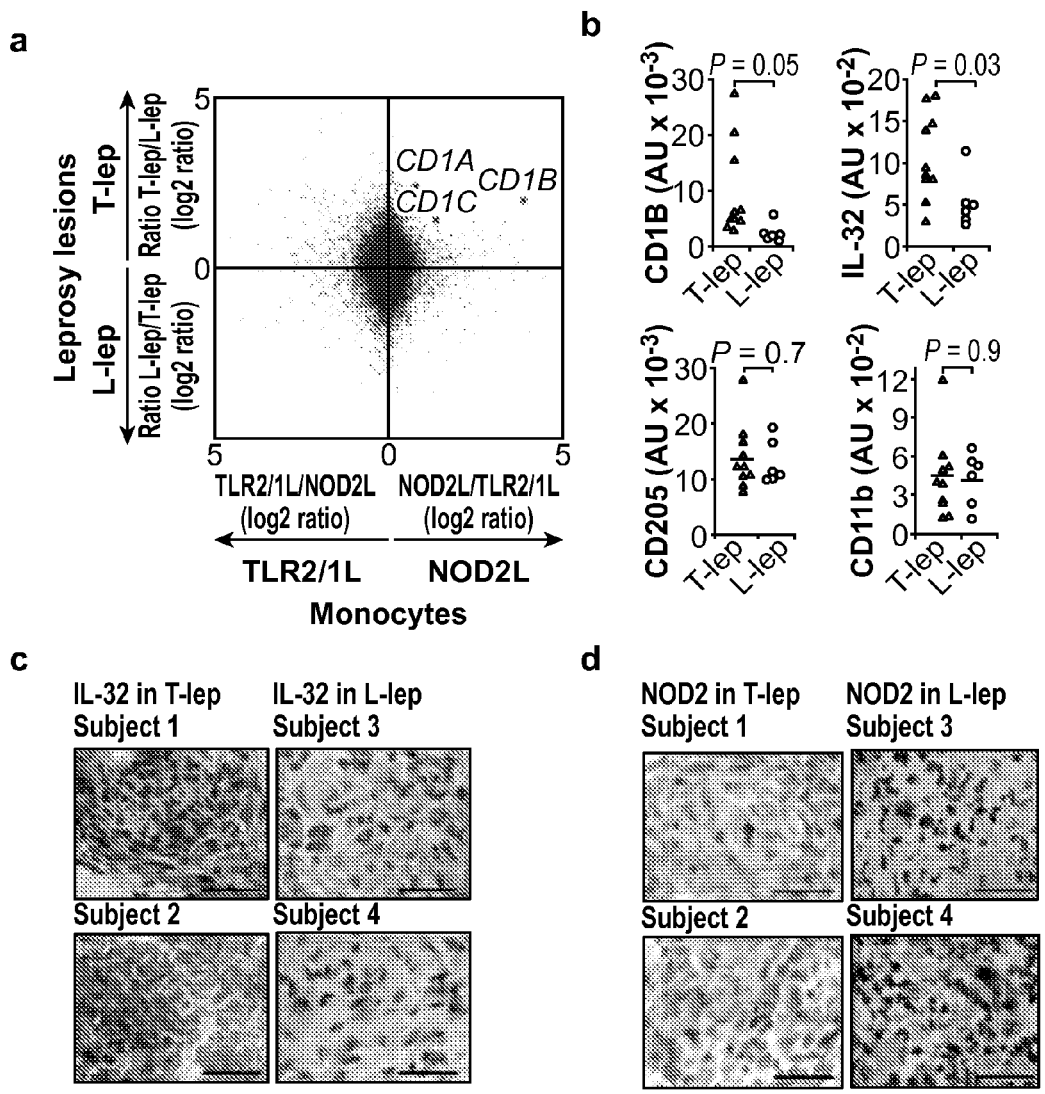
FIG. 5. IL-32 activates a DC program in leprosy. (a) Comparison of gene expression profiles of the microbial ligand-activated monocytes with their differential expression in leprosy skin lesions using an integrative bioinformatics approach. The relative gene expression of NOD2L-versus TLR2/1L-activated monocytes ((log 2) ratio) is shown on the x axis, and the relative expression in T-lep versus L-lep lesions ((log 2) ratio) is shown on the y axis (hypergeometric distribution P=0.004, genes ranked on minimal fold change in the two data sets). (b) Expression of CD1B, IL-32, CD205 and CD11b mRNAs in leprosy lesions according to gene expression profile data. (c,d) Immunolabeling of IL-32 (c) and NOD2 (d) in T-lep and L-lep lesions; two representative labeled sections are shown out of at least six, scale bars, 30 μm. (e) Quantification of IL-32- and NOD2-positive cells in T-lep and L-lep lesions, n=4. (f) Coexpression by confocal laser microscopy of IL-32 with CD68 (macrophages), CD1b (DCs) and NOD2 in T-lep lesions. In b and e, statistical significance was calculated by two-tailed Student's t test.
Figure 5:
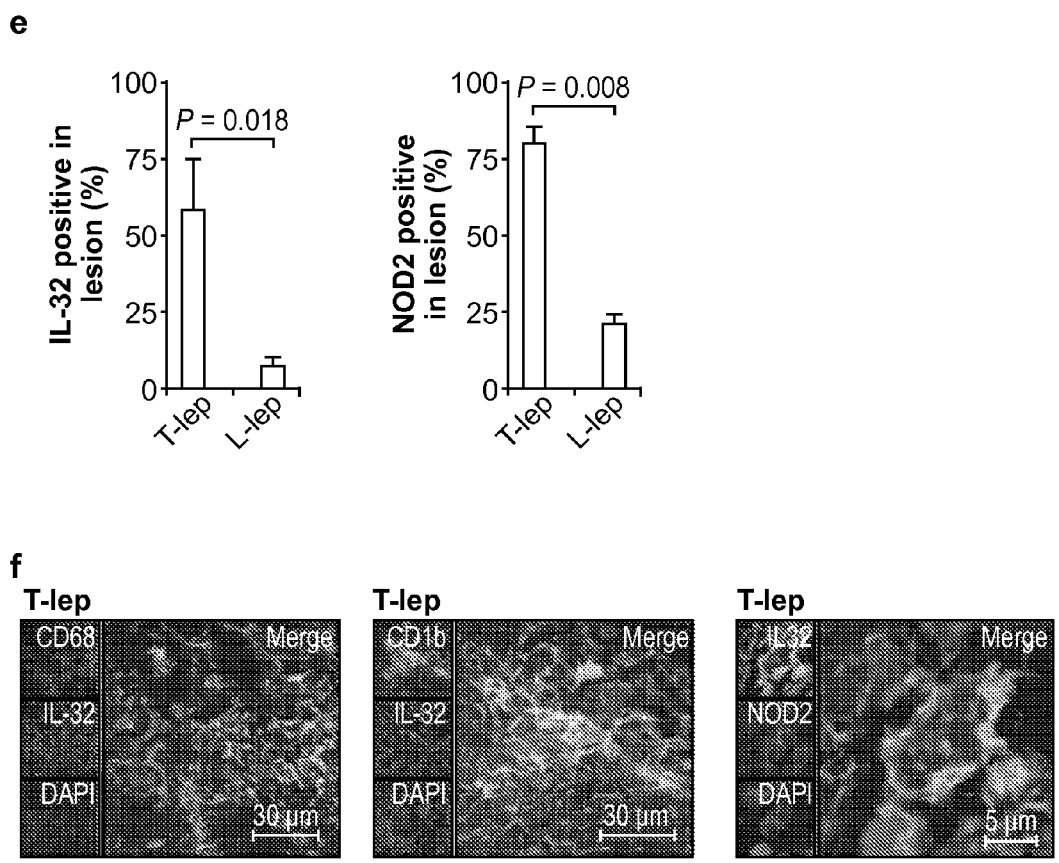

Role of NOD2 and IL-32 in leprosy. To identify which of the NOD2L- and/or TLR2/1L-induced DC-related genes were relevant at the site of infection in human disease, we used an integrative bioinformatics approach. We compared the gene expression in activated monocytes to the gene expression profiles in the skin lesions of the different clinical forms of leprosy. The numbers of lymphocytes and macrophages in leprosy lesions is similar in the different clinical forms, and this has allowed comparison of T cell cytokine patterns in lesions by PCR as well as study of macrophage function using microarrays. The relative induction of all the genes in NOD2L-versus TLR2/1L-activated monocytes was compared to their differential expression at the site of disease in T-lep versus L-lep leprosy (FIG. 5a). Notably, the group I CD1 antigen presentation molecules CD1A, CD1B, and CD1C clustered together, with a high relative expression in both NOD2L- and TLR2/1L-activated monocytes and in T-lep and L-lep lesions. (FIG. 5a). A randomly chosen gene would be unlikely to have the differential expression observed for CD1A, CD1B or CD1C in the two gene expression data sets (P=0.004).

CD1b$^+$ DCs are potent antigen-presenting cells that induce an adaptive immune response in leprosy. Furthermore, the frequency of CD1b+ DCs at the site of disease correlates with clinical form of the disease, as it is higher in T-lep than in L-lep lesions. Examination of the microarray data indicated that the expression of both CD1b and IL-32 mRNA was significantly greater in T-lep versus L-lep lesions (FIG. 5b). In contrast, the gene expression of the DC marker CD205 and the myeloid marker CD11b was similar in the two disease types (FIG. 5b). Consistent with the microarray data, we detected IL-32 protein by immunohistochemistry in granulomas in leprosy lesions, with a higher frequency of positive cells in T-lep as compared to L-lep lesions (FIG. 5c). NOD2-expressing cells were numerous in granulomas of T-lep lesions, whereas only a few NOD2+ cells are found in L-lep lesions (FIG. 5d). Isotype controls were consistently negative (FIG. 28). Quantification using Image J software revealed IL-32+ cells were eightfold more frequent in T-lep versus L-lep lesions, and NOD2+ cells were greater than threefold more frequent in T-lep versus L-lep lesions (FIG. 5e).

We next used confocal laser microscopy to determine the relative localization of IL-32 in relation to macrophages and DCs. We detected IL-32 in proximity to CD68$^+$ macrophages and CD1b$^+$ DCs (FIG. 5f). In addition, NOD2+IL-32+ cells could be detected in T-lep lesions (FIG. 5f). However, this double immunolabeling shows only the relative locations of the various markers and cannot distinguish production from uptake. In summary, the data indicate that IL-32+ cells are more frequent in T-lep versus L-lep lesions.

Figure 6:
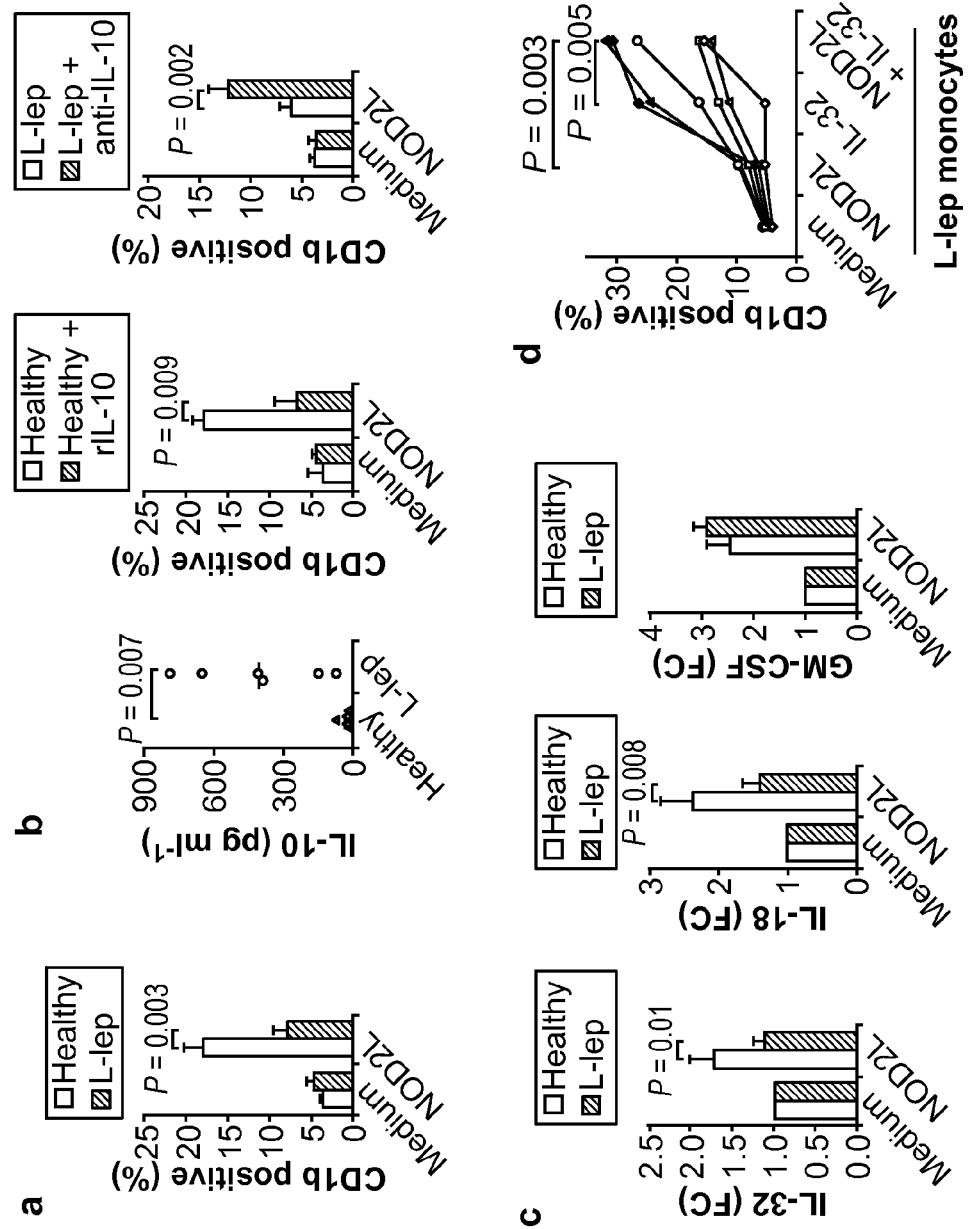
FIG. 6. Monocytes from patients with L-lep show reduced induction of CD1b$^+$ DCs in response to NOD2L compared to healthy controls. (a) Response of monocytes from patients with L-lep and healthy donors to NOD2L (1 μg ml$^{-1}$). (b) Spontaneous IL-10 release in monocytes from patients with L-lep (left), effect of addition of recombinant IL-10 (rIL-10) to normal monocytes on NOD2L-induced CD1b induction (middle) and effect of blocking IL-10 on NOD2L-induced CD1b induction in monocytes from patients with L-lep (right), n=6. (c) IL-32, IL-18 and GM-CSF mRNA induction by NOD2L (1 μg ml$^{-1}$) in monocytes from patients with L-lep. (d) Effect of IL-32 (50 ng ml−1) on CD1b induction by NOD2L (1 μg ml$^{-1}$) in patients with L-lep, n=6. Data are shown as mean±s.e.m., n=6. Statistical significance was calculated by two-tailed Students t test.

Given the low expression of both IL-32 and CD1b in L-lep lesions, we assessed the functional capacity of NOD2 to trigger DC differentiation in monocytes from patients with L-lep. NOD2L activation of monocytes induced a higher frequency of CD1b+ DC expression in normal donors versus patients with L-lep (FIG. 6a). In contrast, GM-CSF treatment of monocytes induced similar numbers of CD1b+ DCs in normal donors and patients with L-lep (FIG. 29). The frequency of CD1b+ DCs induced by treatment of monocytes with NOD2L was equivalent in patients with T-lep and normal donors (FIG. 30).

One possible explanation for the altered responsiveness of monocytes from donors with L-lep to NOD2L could be the release of immunosuppressive factors by monocytes from these individuals. IL-10 is known to be differentially expressed in L-lep versus T-lep lesions and to inhibit immune responses to mycobacteria. Monocytes from patients with L-lep but not healthy controls spontaneously secreted IL-10 into the culture medium (FIG. 6b). The addition of recombinant IL-10 to monocytes from healthy donors inhibited NOD2L-induced CD1b expression (FIG. 6b). Conversely, the addition of IL-10-specific neutralizing antibodies to monocytes from donors with L-lep restored NOD2L-induced CD1b expression (FIG. 6b).

Additionally, we considered the possibility that NOD2L-mediated induction of IL-32 was defective in donors with L-lep. NOD2L induced IL-32 and IL-18 mRNA expression in normal monocytes, but the response was significantly diminished in monocytes from patients with L-lep (FIG. 6c), whereas GM-CSF mRNA was induced to similar levels in monocytes from both normal donors and patients with L-lep (FIG. 6c). Furthermore, NOD2L-mediated induction of GM-CSF and IL-1β proteins was statistically equivalent in normal donors and subjects with L-lep, although NOD2L-mediated induction of tumor necrosis factor-α was greater in monocytes from normal donors than patients with L-lep (FIG. 31). Although NOD2L did not induce appreciable CD1b expression in monocytes from patients with L-lep (FIG. 6d), the addition of recombinant IL-32 alone to monocytes from subjects with L-lep induced CD1b expression to levels similar to those in monocytes from healthy controls. NOD2L and recombinant IL-32 acted synergistically in the induction of CD1b expression in patients with L-lep (FIG. 6d). In conclusion, we provide evidence that NOD2L induces an IL-32-dependent DC program in monocytes with relevance to innate and acquired immune responses in human infectious disease.

The location of PRRs of the innate immune system in specific subcellular compartments provides redundancy in the detection of a given microbe, in that two or more PRRs are activated by a single pathogen, raising the question of whether such activation facilitates detection and determines the magnitude of the innate response or differentially contributes to host defense. We investigated this question using integrative bioinformatics analysis of gene expression profiles of activated monocytes as compared to leprosy lesions with a focus on macrophage and DC differentiation pathways. We found that activation of monocytes by the TLR2/1L (triacylated lipopeptide) but not the NOD2L (MDP) triggers macrophage differentiation, whereas activation of monocytes via NOD2 preferentially triggers DC differentiation. Both live M. leprae and NOD2L but not TLR2/1L induced IL-32, which was required for NOD2-mediated induction of monocyte differentiation into DCs and was also sufficient to induce DC differentiation. In comparing IL-32-versus GM-CSF-differentiated DCs, IL-32-derived DCs expressed higher levels of MHC class I and CD86 and more efficiently presented antigen to MHC class I-restricted CD8+ T cells. Finally, our investigation of skin lesions and peripheral blood monocytes from patients with leprosy provides evidence that activation of the NOD2L-induced IL-32 DC pathway correlates with the self-limited versus the disseminated form of the disease.

Single nucleotide polymorphisms in TLR2, TLR1 and NOD2 genes have implicated these PRRs as key innate immune receptors that contribute to host defense in leprosy. Our data indicate a great redundancy in the TLR2/1- and NOD2-induced responses, in that 3,388 common probes were induced by ligands activating both receptors. Therefore, a single nucleotide polymorphism affecting activation of a particular PRR would not completely block activation of common immune pathways. However, we also found that NOD2L and TLR2/1L activate distinct gene sets, with 1,482 genes specific to NOD2L and 1,100 genes specific to TLR2/1L. These gene sets translated into specific functional pathways, with TLR2/1L inducing an IL-15-dependent macrophage antimicrobial pathway as well as a GM-CSF-dependent DC program and NOD2L inducing a previously unknown IL-32-dependent DC differentiation pathway. Therefore, activation of monocytes via TLR2/1 and NOD2 triggered distinct cell differentiation pathways in addition to their common roles in innate immunity, with TLR2/1 activation contributing to the direct effector functions of the innate immune response via macrophage differentiation and NOD2 activation contributing to the instructive role of the innate immune system on adaptive T cell responses by potently inducing DC differentiation.

A key finding of our study is the identification of a unique pathway of DC differentiation involving the NOD2L-mediated induction of IL-32. NOD2L more strongly induced IL-32 than did TLR2/1L, and it also induced IL-18, which was previously shown to be required for IL-32 induction. Also, NOD2L-induced DC differentiation required IL-32 production, whereas TLR2/1L-induction of DCs was solely dependent on GM-CSF. Notably, our data demonstrate that treatment of primary human monocytes with recombinant IL-32 is sufficient to induce CD1b+ DC differentiation, involving upregulation of the DC markers CD1b, CD40, MHC class I, MHC class II, CD80 and CD86. Immature DCs derived by culture of monocytes with either NOD2L or recombinant IL-32, as compared to either TLR2/1L or recombinant GM-CSF, were characterized by higher expression of MHC class I as well as of CD86 and were more efficient antigen-presenting cells for both particulate antigen (tetanus toxoid) and peptide (influenza M1) in stimulating MHC class I-restricted CD8+ T cell responses. The ability of NOD2L and IL-32 to enhance MHC class I antigen presentation may be relevant to leprosy.

The identification of the NOD2-IL-32 axis in the differentiation of monocytes into DCs provides a new mechanism of innate immunity to microbial pathogens. In addition to inducing monocytes to differentiate into DCs, IL-32 also contributes to the maturation of DCs, which was demonstrated using mouse DCs. The identification of MDP as a mycobacterial ligand that triggers production of IL-32 provides insight into mechanisms by which bacteria and bacterial cell walls are powerful adjuvants in vaccines. The adjuvant activity of MDP may be related to its ability to enhance DC differentiation and function via the NOD2 and IL-32 pathway. The overexpression of IL-32 in the mucosal epithelial cells of individuals with Crohn's disease, a disease with a major susceptibility locus in the NOD2 gene, may contribute to intestinal inflammation.

Finally, monocytes from patients with the progressive L-lep form of leprosy did not respond to NOD2L in terms of IL-32 production and DC differentiation. The mechanism for the altered NOD2 responses has been identified as resulting from the spontaneous release of IL-10, a TH2 cytokine prominent in L-lep lesions. IL-10 is a potent immunosuppressive cytokine, and it blocked NOD2-induced CD1b expression in monocytes from healthy donors. The addition of IL-10-neutralizing antibody or recombinant IL-32 restored DC differentiation. The present studies identify NOD2L-induced IL-32 as a distinct pathway of DC differentiation in humans and provide evidence for the potential use of IL-32 and/or IL-32-derived DCs as immunotherapy for human infectious disease.

Methods

Microbial ligands and cytokines. For activation via NOD2 and TLR2/1, muramyl dipeptide (MDP, Invivogen) and the mycobacterial 19-kDa lipopeptide (EMC Microcollections) were used at 1 μg ml$^{-1}$ each or as indicated. For the differentiation of monocytes with cytokines, IL-32 (50 ng ml$^{-1}$, R&D Systems) and GM-CSF (1 U ml$^{-1}$, 1 U=180 pg, Immunex) were used. These reagents were all tested for endotoxin by LAL Assay (Limulus amoebocyte lysate, Lonza) to be endotoxin free (detection limit <0.1 EU ml$^{-1}$). Other NLR and TLR ligands used were NOD1L (iE-DAP, 10 mg ml$^{-1}$), TLR2/6L (mycoplasma macrophage-activating lipopeptide-2 kDa, 1 μg ml$^{-1}$), TLR4L (lipopolysaccharide, 10 ng ml$^{-1}$), TLR5L (flagellum, 1 μg ml$^{-1}$), TLR7L (imiquimod, 5 μg ml$^{-1}$), TLR8L (single-stranded RNA, 0.5 μg ml$^{-1}$), *M. leprae* sonicate (10 μg ml$^{-1}$), *M. leprae* cell wall (10 μg ml$^{-1}$).

Monocyte isolation, DC differentiation and enrichment. We obtained whole blood from healthy donors (UCLA Institutional Review Board 92-10-591-31) with informed consent. PBMCs were isolated using Ficoll (GE Healthcare) gradient centrifugation, and monocytes were further enriched using Percoll density gradient (GE Healthcare) and subsequent adherence in 1% FCS for 2 h. Monocyte purity was found to be >80%, as measured by CD14 expression. Cells were cultured for 48 h in RPMI and 10% serum, either FCS (Omega Scientific) or human serum. To purify CD1b$^+$ DCs, cells were cultured with the NOD2L, TLR2/1L, recombinant GM-CSF or rIL-32 for 48 h in RPMI with 10% FCS (Omega Scientific), labeled with a CD1b-specific antibody (Bcd3.1, American Type Culture Collection) followed by a microbead-coupled IgG1-specific secondary antibody (Miltenyi Biotec, 130-047-101, 1:5). The positive population was collected using magnetic-activated cell sorting (MACS) according to the manufacturer's recommendations (Miltenyi Biotec). Purity was confirmed to be generally >90% by flow cytometry.

Patients and clinical specimens. All patients with leprosy were recruited with informed consent and approval from the Institutional Review Board of University of Southern California School of Medicine and the Institutional Ethics Committee of Oswald Cruz Foundation. Patients with leprosy were classified according to the criteria of Ridley and Jopling; all patients with T-lep were classified as borderline tuberculoid, and all patients with L-lep had lepromatous leprosy. All T-lep and L-lep biopsy specimens were taken at the time of diagnosis before treatment.

Gene expression profiles. RNA was isolated using Trizol reagent (Invitrogen) and further purified over RNAeasy mini kit columns (Qiagen). Probes were prepared according to the Affymetrix protocol by the UCLA Microarray Core Facility that performed the hybridization of the Affymetrix Human U133 Plus 2.0 array (Affymetrix). Monocytes were isolated from five healthy donors, cultured in RPMI with 10% vitamin D-sufficient (100 nM) human serum and microbial ligands. Medium, NOD2L- and TLR2/1L-stimulated samples were collected at 0 h, 6 h and 24 h. Gene expression analyses were performed as previously described and compared to the gene expression profiles from skin biopsy specimens from a total of 17 patients with leprosy (T-lep, n=10; L-lep, n=7) as previously reported. The acquisition and initial quantification of array images were conducted using the AGCC software (UCLA core, Affymetrix). The subsequent data analysis was performed using Partek v6.4, and further biofunctional analysis was performed using IPA Software. Each gene was ranked by the probability that the means of its expression values are statistically distinct between medium and NOD2L- or TLR2/1L-treated samples using the Student's t test. We focused on genes meeting the criteria P<0.05 and fold change >1.5. Enrichment analysis results were corrected for multiple hypothesis testing using the Benjamini-Hochberg method to control for false discovery. Statistical analysis of differential expression patterns for the group I CD1 antigen presentation molecules were done using the least differentially expressed gene as a upper bound on the significance P value.

Cell surface labeling and ELISA. Cell surface expression of antigenic determinants was determined using epitope-specific antibodies, and cells were acquired and analyzed as described. Fluorochrome-coupled monoclonal antibodies to the following proteins were used: CD40 (BD, 555588, 1:10), HLA-ABC (BD, 555553, 1:10), HLA-DR (BD, 555560, 1:10), CD80 (BD, 557226, 1:10), CD86 (BD, 555658, 1:10) and CD209 (BD, Clone DCN46, 1:10)). For detection of CD1, a monoclonal primary antibody (Bcd3.1, American Type Culture Collection) was used, followed by an IgG1-specific secondary antibody (Invitrogen, A10541, 1:50). Secreted IL-32 protein in the supernatant was measured using an IL-32 Sandwich ELISA kit (SEL101, YbdYbiotech, Korea).

T cell assays. For investigation of MHC class II-restricted antigen presentation to T cells, monocytes were differentiated into immature DCs and enriched for CD1b$^+$ cells (as described above). Purified DCs were cultured with the MHC class II-restricted T cell clone derived from a patient with T-lep (1×10$^5$, BCD4.9) that recognized the *M. leprae* GroES protein and a defined peptide spanning amino acids 28-39 in an HLA-DR15-restricted manner. IFN-γ was measured by ELISA (BD Pharmingen), and proliferation was measured using 3H-thymidine incorporation as described. For MHC class I-restricted antigen presentation studies, CD1b$^+$ DCs were prepared as above from tetanus toxoid-immunized healthy donors, under informed consent and approval from the UCLA IRB and the potential to present tetanus toxoid antigen (10 μg ml$^{-1}$) to autologous CD8$^+$ T cells was assessed (see above). The response of auto CD8$^+$ T cells to influenza peptide M158-66 (10 μg ml$^{-1}$, Princeton Biomolecules) was tested. In some experiments, the efficiency of antigen presentation by DCs was evaluated by performing titrations, varying the number of antigen-presenting cells, using an optimal concentration of antigen. The control without antigen performed at the highest concentration of CD1b$^+$ DCs is shown for each experiment. The mean values from proliferation assays and IFN-γ ELISA were always more than sevenfold greater in cultures with antigen versus medium control.

Real-time quantitative PCR. Following stimulation, RNA was isolated using Trizol (Invitrogen); cDNA and quantitative PCR performed as previously described. Quantitect primers (Qiagen) were used. The relative quantities of the gene tested per sample were calculated against 36B4 using the Δ cycle threshold formula as previously described (isolated RNA and synthesized cDNA as described). The data were normalized by fold change to medium control samples.

Immunoperoxidase and immunofluorescence. Immunoperoxidase and double immunofluorescence labeling on leprosy skin lesions was performed and examined as described. Monoclonal antibodies against IL-32 (A11C9, YbdYbiotech, 1:200), CD1b (Bcd3.1, ATCC, 1:50), CD68 (EBM11, Dako, 1:100) and NOD2 (2D9, Thermo Scientific, 1:20) were used.

Mycobacterial ligands. The in vitro system studied here involves the exogenous addition of ligands as opposed to the in vivo intracellular infection. However, the differences between NOD2L vs. TLR2/1L responses were consistent over a range of ligand doses. The NOD2/1L used for these studies was *E. coli* MDP, which was readily available in highly purified form and as shown, induced IL-32 expression. The *E. coli* MDP is glycolated and known to more potently stimulate TNF responses as compared to the non-glycolated forms present in some mycobacteria. However, unlike other *Mycobacterium* spp. the muramic acid of mLEP is exclusively N-acetylated. mLEP lacks a functional namH gene responsible for N-glycolylmuramic acid biosynthesis. Differences do occur between the peptides linked to the N-acetyl muramic acid of *E. coli* and mLEP. The TLR2/1 ligand employed was a synthetic triacylated lipopeptide containing the first six amino acids of the *M. tuberculosis* 19 kD lipoprotein. Previous studies indicate that the mLEP and *M. tuberculosis* lipoproteins are equally potent inducers of monocyte cytokine responses. Diacylated lipopeptides activate TLR2/6 and are equipotent as triacylated lipopeptides in activating monocyte cytokine responses and differentiation.

What is claimed is:

1. A method of inducing dendritic cell differentiation from a mammalian precursor cell, the method comprising:

contacting a population of human monocytes with an effective dose of IL-32, for a period of time sufficient to induce differentiation of the precursor cells into dendritic cells wherein the contacting is performed ex vivo; and isolating CD1b positive dendritic cells from said population.

2. The method of claim 1, wherein the IL-32 is a human IL-32 protein.

3. The method of claim 1, wherein the contacting is performed in the presence of an antigen of interest.

4. The method of claim 1, wherein the human monocytes are isolated from a biological sample of peripheral blood mononuclear cells.

5. The method of claim 1, wherein the dendritic cells are infused into an individual in need of increased immune responsiveness.

6. The method of claim 5, wherein the dendritic cell is autologous or allogeneic with respect to the individual.

* * * * *